(12) United States Patent
Iwakura et al.

(10) Patent No.: US 8,038,945 B2
(45) Date of Patent: Oct. 18, 2011

(54) DETECTION AND ANALYSIS SYSTEM FOR PROTEIN ARRAY

(75) Inventors: Masahiro Iwakura, Tsukuba (JP); Kiyonori Hirota, Tsukuba (JP); Hisashi Takahashi, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 759 days.

(21) Appl. No.: 11/792,095

(22) PCT Filed: Dec. 2, 2005

(86) PCT No.: PCT/JP2005/022213
§ 371 (c)(1),
(2), (4) Date: Apr. 22, 2008

(87) PCT Pub. No.: WO2006/059727
PCT Pub. Date: Jun. 8, 2006

(65) Prior Publication Data
US 2008/0261827 A1    Oct. 23, 2008

(30) Foreign Application Priority Data
Dec. 3, 2004    (JP) .................................. 2004-351446

(51) Int. Cl.
*G01N 21/00*    (2006.01)
(52) U.S. Cl. ........................ 422/82.05; 435/7.92; 506/12
(58) Field of Classification Search .......................... None
See application file for complete search history.

(56) References Cited

U.S. PATENT DOCUMENTS

| | | | |
|---|---|---|---|
| 5,542,012 A | 7/1996 | Fernandes et al. | |
| 6,001,587 A * | 12/1999 | Turner et al. | 435/41 |
| 6,229,603 B1 | 5/2001 | Coassin et al. | |
| 6,686,582 B1 | 2/2004 | Volcker et al. | |
| 2003/0054176 A1 * | 3/2003 | Pantano et al. | 428/429 |
| 2003/0148295 A1 * | 8/2003 | Wan et al. | 435/6 |
| 2004/0009528 A1 | 1/2004 | Shaw et al. | |
| 2004/0014242 A1 | 1/2004 | Iwakura et al. | |

FOREIGN PATENT DOCUMENTS

| | | |
|---|---|---|
| JP | 2003-344396 | 12/2003 |
| JP | 2004-325172 A | 11/2004 |
| WO | WO 99/23474 | 5/1999 |
| WO | WO 2004007669 A2 * | 1/2004 |
| WO | WO 2004/007669 A2 | 2/2004 |

* cited by examiner

*Primary Examiner* — Ann Lam
(74) *Attorney, Agent, or Firm* — Stephen A. Bent; Foley & Lardner LLP

(57) ABSTRACT

To provide a method for detecting a protein by immobilizing a protein on a protein array substrate at a high density with controlled orientation, irradiating the immobilized protein with ultraviolet light, visible light, or infrared light, and measuring the light not absorbed by the protein and further analyzing an interaction between the protein on the substrate and another protein and/or a compound other than proteins, a system used for the method, and to provide a protein array suitable for the system. A system including a protein array in which a protein is immobilized in aligned position on a light-transmissive substrate at a high density, a light-irradiating means, and a light-detecting means and being for detecting or analyzing a protein on the protein array and/or a compound which is other than proteins and interacts with the immobilized protein, wherein the protein array is irradiated with light by the light-irradiating means, and the light transmitted through the protein array is measured by the light-detecting means for detecting the light absorption of the protein on the protein array and/or the compound which is other than proteins and interacts with the immobilized protein.

22 Claims, 9 Drawing Sheets
(3 of 9 Drawing Sheet(s) Filed in Color)

(1): Mirror 1
(2): Cell holder
(3): Mirror 2
(4): CCD camera (the gain of the CCD element is adjusted by using the attached application)

SEQUENCE LISTING

<160> NUMBER OF SEQ ID NOS: 7

<210> SEQ ID NO 1
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn
225                 230                 235

```
<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Gly Gly Cys Ala Asp Asp Asp Asp Asp Asp
1               5                   10

<210> SEQ ID NO 3
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Asn Gly
225                 230                 235                 240

Gly Gly Gly Gly Gly Cys Ala Asp Asp Asp Asp Asp Asp
                245                 250

<210> SEQ ID NO 4
<211> LENGTH: 159
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 4

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Ala Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Ser Phe Glu Ile Leu Glu Arg Arg
145                 150                 155

<210> SEQ ID NO 5
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Ala Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Ser Phe Glu Ile Leu Glu Arg Arg Gly
145                 150                 155                 160

Gly Gly Gly Cys Ala Asp Asp Asp Asp
                165

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Cys Ala Asp Asp Asp Asp
 1               5                  10

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly
 1
```

DETECTION AND ANALYSIS SYSTEM FOR PROTEIN ARRAY

The application contains at least one drawing executed in color. Copies of this patent or patent application publication with color drawing(s) will be provided by the Office upon request and payment of the necessary fee.

TECHNICAL FIELD

The present invention relates to a system for detecting or analyzing a protein on a protein array on which the protein immobilized in aligned position at a high density or an interaction between the protein and another protein and/or a compound other than proteins by measuring ultraviolet, visible, or infrared light absorption of the protein using a spectrophotometer.

BACKGROUND ART

A protein array (protein chip) is a technology providing new possibilities as a means for investigating functions of unknown proteins encoded by genes or analyzing complicated interactions among a large number of proteins at once. The protein array is provided by aligning a protein or a peptide on a substrate, and various protein arrays have been reported (see Patent Documents 1 and 2). In protein array technology, a protein is immobilized on an appropriate substrate, the immobilized protein is brought into interaction with another protein or the like, and the interacting spots on the array are detected.

The detection of spots on an array is carried out by using a compound labeled with a fluorescent dye or the like and capable of interacting with the immobilized protein and measuring the fluorescence emission from the fluorescent dye on the array. This method, however, requires preparing a label preparation and has the problem that the activity of a protein may be decreased by labeling of the protein. In addition, equipment for measuring an array using a fluorescence-measuring device or the like is not widely used. Further, the interaction between proteins cannot be analyzed in real time.

In order to solve these problems, a detection process by surface plasmon resonance (SPR) imaging has been developed (see Non-Patent Documents 1 and 2). In this process, a protein immobilized on a protein array is detected by irradiating the array with a polarized beam to give an SPR image of the reflected light and analyzing the reflection light intensity of the SPR image. This process has advantages that a label is not required and that the detection can be performed in real time. However, the interaction between an immobilized protein and a low-molecular substance cannot be analyzed even if the SPR imaging process is employed, and also this process has the problem that the dynamic range is narrow. In addition, there are problems that equipment used for SPR imaging is extremely expensive and that construction of a detection system is not easy.

Further, though a detection process using a protein array having a crystal oscillator integrated thereinto has been reported (see Non-Patent Document 3), this process has the same problems as in the above-described SPR imaging process.

In addition, though a detection process utilizing microscopic Fourier transform infrared spectroscopy (micro FT-IR) has been reported (see Patent Document 3), the measurement apparatus is expensive, and the process is not necessarily suitable for quantitative determination.

[Patent Document 1] JP Patent Publication (Kohyo) No. 2002-520618A
[Patent Document 2] JP Patent Publication (Kohyo) No. 2002-502038A
[Patent Document 3] JP Patent Publication (Kokai) No. 2004-45390A
[Non-Patent Document 1] Nelson, B. P., et al., Anal. Chem., 71(18), 3928-3934 (1999)
[Non-Patent Document 2] Brockman, J. M., et al., Annu. Rev. Phys. Chem., 51, 41-63 (2000)
[Non-Patent Document 3] Y. Okahata, et al., J. Am. Chem. Soc., 114, 8299-8300 (1992)

DISCLOSURE OF THE INVENTION

It is an object of the present invention, in order to solve the above-mentioned problems on conventionally used protein arrays and detection/analysis systems using protein arrays, to provide a method and a system therefor for detecting a protein on an array substrate and further analyzing the interaction between the protein on the substrate and another protein and/or a compound other than proteins by immobilizing the protein on the array substrate at a high density with controlled orientation, irradiating the immobilized protein with ultraviolet light, visible light, or infrared light, and measuring the light not absorbed by the protein. Further, it is an object of the present invention to provide a protein array suitable for the system. In particular, it is an object of the present invention to provide a method and a system therefor for detecting a protein on an array substrate and further analyzing the interaction between the protein on the substrate and another protein or a compound other than proteins, in particular, an interaction between the protein and a low molecular compound which can interact with the protein by using an ultraviolet light-transmissive substrate as the array substrate, irradiating the substrate to which the protein immobilized with ultraviolet light, and measuring the ultraviolet light not absorbed by the protein. Further, it is an object of the present invention to provide a protein array suitable for the system.

The present inventors have conducted intensive investigations, taking the above-mentioned problems into consideration, for developing a system for detecting or analyzing the interaction between a protein and a protein and/or another substance by using a protein array utilizing equipment which does not require labeling the protein with a fluorescent dye or the like and is inexpensive and readily available.

In conventional methods, characteristically, a protein is immobilized on an array substrate in femto- to picomole quantities for detecting a very small amount of an analyte; a label such as a fluorescent dye is used for detecting a very small amount of protein; or a system which needs a specific apparatus such as SPR is used. The present inventors completed a method for immobilizing a protein on an array substrate at a high density with controlled orientation (JP Patent Nos. 2517861, 2990271, and 3047029, JP Patent Publication (Kokai) No. 2003-344396A, and so on). According to this method, a protein can be immobilized on a substrate in the order of nmol/cm$^2$ which is ten to hundred times greater than the conventional amount. The present inventors have found the fact that this protein array to which a protein is immobilized at a high density allows to measure the protein on the array by measuring optical activity of the protein with a spectrophotometer which is widely used and is relatively inexpensive, without labeling the protein with a fluorescent dye and using an expensive apparatus. In other words, since a large amount of a protein is immobilized on a substrate at a high density, when the immobilized protein is irradiated with light having a wavelength which is absorbed by the protein or a substance which interacts with the immobilized protein, the irradiated light is absorbed by the protein or the substance interacts with the protein on the array. The light absorbed by the immobilized protein or the substance which interacts with the protein can be determined by measuring the intensity of the transmitted light without being absorbed by the protein or the substance. That is, the present inventors have found the fact that a protein on an array or a substance which interacts with the protein can be directly measured by utilizing its optical activity. In particular, since proteins absorb ultraviolet light, the ultraviolet light not absorbed by a protein can be measured as light transmitted through the array substrate on which the protein is immobilized by using an ultraviolet light-transmissive substrate such as quartz glass. Here, in order to measure the transmission of light at each protein spot immobilized on an array substrate at once, it is desirable to use a two-dimensional photodetector such as a CCD. However, a two-dimensional photodetector which can detect ultraviolet light is extremely expensive. Therefore, a system using such a photodetector cannot be readily constructed. Hence, the present inventors have completed the present invention by converting ultraviolet light transmitted through a substrate on which a protein is immobilized into visible light with an ultraviolet-visible light converting device such as fluorescent glass so that a CCD which is inexpensive and readily available can be used.

That is, the aspects of the present invention are as follows:
(1) a system comprising a protein array in which a protein is immobilized in aligned position on a light-transmissive substrate at a high density and a spectrophotometer, the system being for detecting or analyzing a protein on the protein array and/or a compound which is other than proteins and interacts with the immobilized protein, wherein the protein on the protein array and/or the compound other than proteins are detected/analyzed by irradiating the protein array with light and measuring the light transmitted through the protein array using the spectrophotometer for determining the light absorption of the protein on the array and/or the compound which is other than proteins and interacts with the immobilized protein;
(2) a system comprising a protein array in which a protein is immobilized in aligned position on a light-transmissive substrate at a high density, a light-irradiating means, and a light-detecting means, the system being for detecting or analyzing a protein on the protein array and/or a compound which is other than proteins and interacts with the immobilized protein, wherein the protein on the protein array and/or the compound other than proteins are detected/analyzed by irradiating the protein array with light by the light-irradiating means, measuring the light transmitted through the protein array by the light-detecting means for determining the light absorption of the protein on the array and/or the compound which is other than proteins and interacts with the immobilized protein;
(3) the system for detecting or analyzing a protein on a protein array and/or a compound which is other than proteins and interacts with the immobilized protein according to the above (2), the system further comprising a data-processing means;
(4) the system for detecting or analyzing a protein on a protein array and/or a compound which is other than proteins and interacts with the immobilized protein according to any one of the above (1) to (3), wherein the protein is immobilized at a density of 0.01 µg/mm$^2$ or more per spot of the protein array;
(5) the system for detecting or analyzing a protein on a protein array and/or a compound which is other than proteins and interacts with the immobilized protein according to any one of the above (1) to (3), wherein the protein is immobilized at a density in such a manner that the absorbance of each spot of the protein array is 0.001 or more;
(6) the system for detecting or analyzing a protein on a protein array and/or a compound which is other than proteins and interacts with the immobilized protein according to any one of the above (1) to (5), wherein the protein immobilized in aligned position at a high density is represented by the formula $NH_2-R_1-CO-NH-R_2-CO-NH-Y$, wherein $R_1$ and $R_2$ each denote an optional amino acid sequence, and Y denotes a substrate;
(7) the system for detecting or analyzing a protein on a protein array and/or a compound which is other than proteins and interacts with the immobilized protein according to any one of the above (1) to (6), wherein the protein is immobilized in aligned position by a covalent bond between a carrier containing a primary amine cast on a surface of light-transmissive glass and a carboxy group at the C-terminus of the amino acid sequence of the protein;
(8) the system for detecting or analyzing a protein on a protein array and/or a compound which is other than proteins and interacts with the immobilized protein according to any one of the above (1) to (7), wherein the light-detecting means is a CCD or a photodiode array;
(9) the system for detecting or analyzing a protein on a protein array and/or a compound which is other than proteins and interacts with the immobilized protein according to any one of the above (1) to (8), wherein the light irradiated to the protein array is ultraviolet light, and the light-transmissive substrate is an ultraviolet light-transmissive substrate;
(10) the system for detecting or analyzing a protein on a protein array and/or a compound which is other than proteins and interacts with the immobilized protein according to the above (9), wherein the ultraviolet light-transmissive substrate is a quartz glass substrate;
(11) the system for detecting or analyzing a protein on a protein array and/or a compound which is other than proteins and interacts with the immobilized protein according to the above (9) or (10), wherein an ultraviolet-visible light converting device is irradiated with the ultraviolet light transmitted through the protein array, and the visible light converted from the ultraviolet light is detected;
(12) the system for detecting or analyzing a protein on a protein array and/or a compound which is other than proteins and interacts with the immobilized protein according to the above (11), wherein the ultraviolet-visible light converting device is fluorescent glass;
(13) the system for detecting or analyzing a protein on a protein array and/or a compound which is other than proteins and interacts with the immobilized protein according to any one of the above (1) to (12), wherein a protein in a sample, the protein interacting with the immobilized protein, and/or a compound in a sample, the compound being other than proteins and interacting with the immobilized protein, is detected by bringing the sample into contact with the immobilized protein on the protein array and measuring the light absorption of the protein on the protein array and/or the compound which is other than proteins and interacts with the immobilized protein before and after the contact;
(14) the system for detecting or analyzing a protein on a protein array and/or a compound which is other than proteins and interacts with the immobilized protein according to any one of the above (1) or (12), wherein an interaction between the immobilized protein and another protein or a compound other than proteins is analyzed by bringing the another protein and/or the compound which is other than proteins and interacts with the immobilized protein into contact with the immobilized protein on the protein array and measuring the light absorption of the protein on the protein array and/or the compound which is other than proteins and interacts with the immobilized protein over before and after the contact;
(15) the system for detecting or analyzing a protein on a protein array and/or a compound which is other than proteins and interacts with the immobilized protein according to any one of the above (1) or (12), wherein the light-transmissive substrate is a flow channel cell or microchip provided with a channel therein, the protein is immobilized in the channel, and an interaction between the immobilized protein and a protein and/or compound in a sample, the compound being other than proteins and interacting with the immobilized protein, is analyzed by letting the sample flow in the channel;
(16) a method for detecting or analyzing a protein on a protein array and/or a compound which is other than proteins and interacts with an immobilized protein, wherein the protein array in which a protein is immobilized in aligned position on a light-transmissive substrate at a high density is irradiated with light by using a spectrophotometer, and the light transmitted through the protein array is measured for determining the light absorption of the protein on the array and/or the compound which is other than proteins and interacts with the immobilized protein;
(17) the method for detecting or analyzing a protein on a protein array and/or a compound which is other than proteins and interacts with an immobilized protein according to the above
(16), wherein the protein is immobilized at a density of 0.01 $\mu g/mm^2$ or more per spot of the protein array;
(18) the method for detecting or analyzing a protein on a protein array and/or a compound which is other than proteins and interacts with an immobilized protein according to the above (16), wherein the protein is immobilized at a density in such a manner that the absorbance of each spot of the protein array is 0.001 or more;
(19) the method for detecting or analyzing a protein on a protein array and/or a compound which is other than proteins and interacts with the immobilized protein according to any one of the above (16) to (18), wherein the protein immobilized in aligned position at a high density is represented by the formula $NH_2—R_1—CO—NH—R_2—CO—NH—Y$, wherein $R_1$ and $R_2$ each denote an optional amino acid sequence, and Y denotes a substrate;
(20) the method for detecting or analyzing a protein on a protein array and/or a compound which is other than proteins and interacts with the immobilized protein according to any one of the above (16) to (19), wherein the protein is immobilized in aligned position by a covalent bond between a carrier containing a primary amine cast on a surface of light-transmissive glass and a carboxy group at the C-terminus of the amino acid sequence of the protein;
(21) the method for detecting or analyzing a protein on a protein array and/or a compound which is other than proteins and interacts with the immobilized protein according to any one of the above (16) to (20), wherein the light-detecting means is a CCD or a photodiode array;
(22) the method for detecting or analyzing a protein on a protein array and/or a compound which is other than proteins and interacts with the immobilized protein according to any one of the above (16) to (21), wherein the light irradiated to the protein array is ultraviolet light, and the light-transmissive substrate is an ultraviolet light-transmissive substrate;
(23) the method for detecting or analyzing a protein on a protein array and/or a compound which is other than proteins and interacts with the immobilized protein according to the above (22), wherein the ultraviolet light-transmissive substrate is a quartz glass substrate;
(24) the method for detecting or analyzing a protein on a protein array and/or a compound which is other than proteins and interacts with the immobilized protein according to the above (22) or (23), wherein an ultraviolet-visible light converting device is irradiated with the ultraviolet light transmitted through the protein array, and the visible light converted from the ultraviolet light is detected;
(25) the method for detecting or analyzing a protein on a protein array and/or a compound which is other than proteins and interacts with the immobilized protein according to the above (24), wherein the ultraviolet-visible light converting device is fluorescent glass;
(26) the method for detecting or analyzing a protein on a protein array and/or a compound which is other than proteins and interacts with the immobilized protein according to any one of the above (16) to (25), wherein a protein in a sample, the protein interacting with the immobilized protein, and/or a compound in a sample, the compound being other than proteins and interacting with the immobilized protein, is detected by bringing the sample into contact with the immobilized protein on the protein array and measuring the light absorption of the protein on the protein array and/or the compound which is other than proteins and interacts with the immobilized protein before and after the contact;
(27) the method for detecting or analyzing a protein on a protein array and/or a compound which is other than proteins and interacts with the immobilized protein according to any one of the above (16) or (25), wherein an interaction between the immobilized protein and another protein or a compound other than proteins is analyzed by bringing the another protein or the compound which is other than proteins and interacts with the immobilized protein into contact with the immobilized protein on the protein array and measuring the light absorption of the protein on the protein array and/or the compound which is other than proteins and interacts with the immobilized protein over before and after the contact;
(28) the method for detecting or analyzing a protein on a protein array and/or a compound which is other than proteins and interacts with the immobilized protein according to any one of the above (16) or (25), wherein the light-transmissive substrate is a flow channel cell or microchip provided with a channel therein, the protein is immobilized in the channel, and an interaction between the immobilized protein and a protein and/or compound, the compound being other than proteins and interacting with the immobilized protein, is analyzed by letting the sample flow in the channel;
(29) a protein array comprising a protein and a substrate represented by the formula $NH_2—R_1—CO—NH—R_2—CO—NH—Y$, wherein $R_1$ and $R_2$ each denote an optional amino acid sequence, and Y denotes the substrate, wherein the protein is immobilized in aligned position on the substrate at a high density and the substrate is made of light-transmissive glass;
(30) the protein array according to the above (29), wherein the light-transmissive glass is ultraviolet light-transmissive glass;
(31) the protein array according to the above (30), wherein the ultraviolet light-transmissive glass is quartz glass;
(32) the protein array according to any one of the above (29) to (31), wherein the protein is immobilized at a density of 0.01 $\mu g/mm^2$ or more per spot of the protein array;
(33) the protein array according to any one of the above (29) to (31), wherein the protein is immobilized at a density in such a manner that the absorbance of each spot of the protein array is 0.001 or more; and
(34) the protein array according to any one of the above (29) to (33), wherein the protein is immobilized in aligned position by a covalent bond between a carrier containing a primary amine cast on a surface of light-transmissive glass and a carboxy group at the C-terminus of the amino acid sequence of the protein.

In the protein array used in the present invention, a protein is immobilized on a light-transmissive substrate at a high density with controlled orientation. Therefore, the light absorbed by the protein can be determined by irradiating the substrate with light and measuring light transmitted through the substrate. Further, the amount of the protein on the protein array can be measured using this light absorption. Therefore, a substance labeled with a fluorescent dye or the like is not necessary for the detection, unlike conventional methods. In addition, the amount of a protein on the protein array can be directly determined by measuring optical activity of the protein. Further, in the present invention, since ultraviolet light, visible light, or infrared light is measured, the amount of a protein on a protein array can be readily measured using a spectrophotometer which is widely used. In particular, a protein on the protein array can be precisely measured using ultraviolet absorption which is generally carried out as a method for quantifying proteins. Furthermore, a protein at each spot on the protein array can be rapidly measured at once by using a two-dimensional photodetector, such as a CCD, as the light-detecting means. In addition, a CCD for digital cameras, which is inexpensive and readily available, can be adopted by using an ultraviolet light-transmissive substrate and fluorescent glass and the like capable of converting ultraviolet light into visible light. Consequently, the cost for constructing a system is low.

In addition, an interaction such as binding of a protein to another protein or a compound other than proteins can be analyzed by measuring a change in the light absorption of the protein on the protein array or light absorption of the compound other than proteins.

Figure 1:
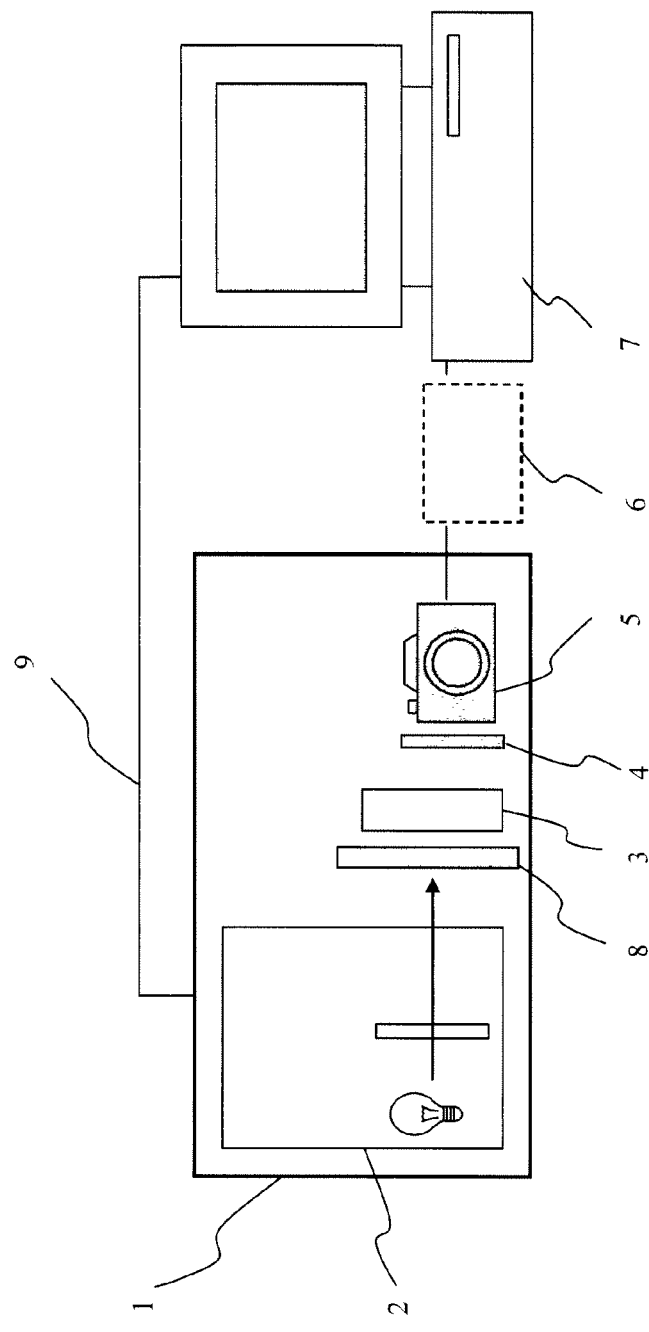
FIG. 1 is a diagram showing a system according to the present invention.

DESCRIPTION OF SYMBOLS 1 spectrophotometer
2 optical unit (light-irradiating means)
3 protein-immobilizing light-transmissive substrate
4 ultraviolet-visible light converting device
5 CCD camera (light-detecting means)
6 video capture board
7 data-processing means
8 lens or slit
9 communication means
10 array substrate
11 immobilized protein
12 cover
13 intake port
14 exhaust port
15 synthetic quartz glass
16 matrix
17 fluorescent glass
18 spot
19 light cross section

BEST MODE FOR CARRYING OUT THE INVENTION

In the detection or analysis system for a protein array according to the present invention, a protein is detected/analyzed by using a substrate on which a protein is immobilized at a high density, irradiating the protein on the substrate with light (ultraviolet light, visible light, or infrared light), and directly measuring the light absorption of the protein on the substrate. Further, in the system according to the present invention, the substrate is an ultraviolet light-transmissive one, and a protein is detected/analyzed by utilizing the absorption of ultraviolet light of the protein. Here, the term "detection/analysis" refers to qualitative or quantitative analysis of a protein, measurement of the interaction between a protein and another protein or a compound other than proteins, measurement of the protein-ligand interaction based on a change in the absorbance of an immobilized protein, monitoring of a structural change in the protein itself, and qualitative or quantitative analysis of a compound which is other than proteins and interacts with an immobilized protein.

In the present invention, the term protein is used so as to include peptides and polypeptides. In addition, the term "protein on the array" when a protein on an array is detected is used to include not only proteins immobilized on the array via an NH group but also other proteins bound to the immobilized proteins via the interaction therebetween. Further, the term "detection/analysis of a protein on the array" is used to include not only detection/analysis of a protein immobilized on the array or another protein which interacts with the immobilized protein but also detection/analysis of a structural change or the like of the above-mentioned proteins. The structural change is caused by the interaction between the protein immobilized on the array and a compound other than proteins, for example, a low molecular compound and causes a change in the absorption. Thus, the structural change can be detected/analyzed by measuring this absorption change. In addition, the term "detection/analysis of another compound interacted with a protein on the array" refers to detection/analysis of a compound which is other than proteins and interacts with a protein immobilized on the array and refers to measurement of the compound by using light having a wavelength which is specifically absorbed by the compound.

FIG. 1 shows a configuration of a detection or analysis system for a protein array according to the present invention. The system includes a system-controlling unit containing a light-irradiating means (optical unit) 2; a measurement unit containing a light-detecting means 5 such as a CCD digital camera and, if necessary, a video data processing means 6 such as a video capture board; data processing unit 7; and a light-transmissive substrate 3 on which a protein is immobilized at a high density. The measurement unit may contain an ultraviolet-visible light converting device 4. In addition, a lens or a slit 8 may be provided on an optical path from the optical unit 2 to the substrate 3. Further, the data processing means can control the operation of the system-controlling unit with a communication means 9 such as RS232C. In this system, a spectrophotometer 1 is a unit including a light-irradiating means and a light-detecting means and having functions for generating light, dispersing the light, irradiating the protein array with the light, and measuring transmitted light. Thus, the present invention can further provide a system for detecting a protein on a light-transmissive substrate on which a protein is immobilized at a high density using a spectrophotometer. Here, the spectrophotometer is an apparatus for measuring infrared, visible, or ultraviolet spectra. In the present invention, an ultraviolet spectrum is preferably measured. Therefore, an ultraviolet-visible spectrophotometer, which is widely used, can be used.

Figure 2:
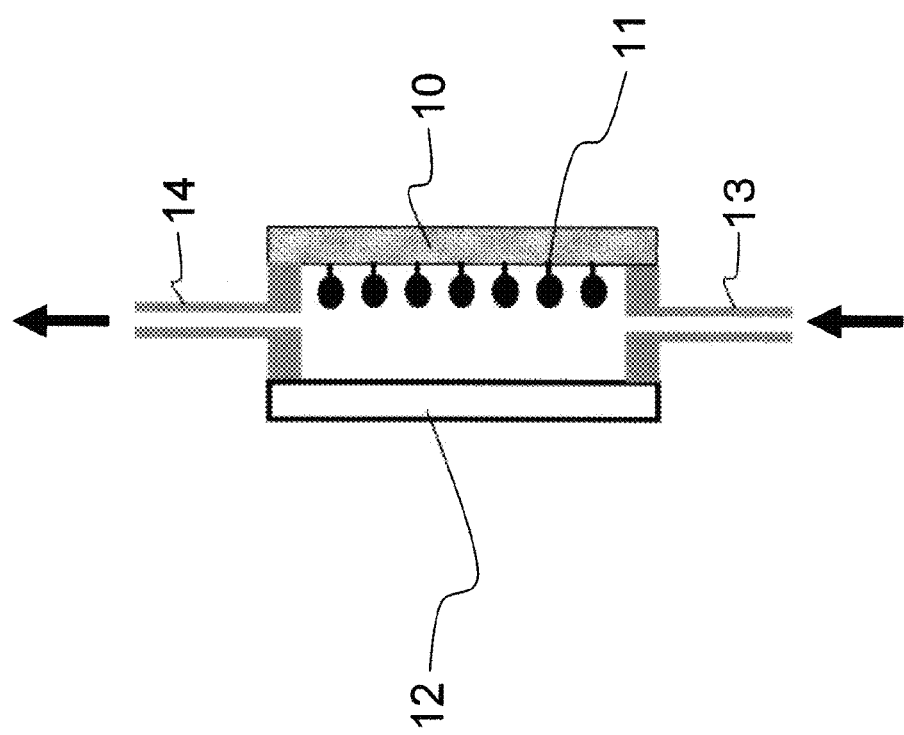
FIG. 2 is a diagram schematically showing a flow unit which is placed in the position of the protein-immobilizing light-transmissive substrate 3 in FIG. 1.

In the present invention, since the protein immobilized on a substrate is irradiated with light and light absorption of the protein is directly measured, the substrate is necessarily light-transmissive. The term "light-transmissive" refers to a property transmitting ultraviolet light, visible light, or infrared light, namely, a property not absorbing these beams of light. Therefore, the substrate is desirably transparent, and examples of which include transparent glass (such as quartz glass and Pyrex glass) and transparent plastic. When the measurement is conducted using ultraviolet light, the substrate is necessarily ultraviolet light-transmissive. The ultraviolet light-transmissive substrate may be a glass substrate which is made of the same material, such as ultraviolet light-transmissive glass, as that of a cell (cuvette) used in a spectrophotometer for measuring ultraviolet light or may be a slide glass made of quartz glass such as synthetic quartz glass or fused quartz glass. Synthetic quartz glass (for example, manufactured by Shin-Etsu Chemical) is preferable. Further, the present invention provides a flow unit for measuring the interaction between the protein immobilized on a substrate and another protein or a compound other than proteins in liquid. FIG. 2 schematically shows such a flow unit. The flow unit can be readily fabricated by sandwiching a glass substrate (array substrate 10) on which a protein 11 is immobilized with a cover glass substrate (cover 12) using appropriate spacers and forming a solution inlet (intake port 13) in one of the spacer and a solution outlet (exhaust port 14) in the other spacer so that a solution flows from the outside. The flow unit is mounted on the position of the protein-immobilizing light-transmissive substrate 3 of the system shown in FIG. 1. The flow unit can also be constructed by using a microchip or the like having a flow channel cell or a glass substrate provided with a channel with high precision in the order of micrometer and immobilizing a protein on the glass in the channel. When a microchip is used, the microchip may be fabricated by forming a channel substrate provided with a channel and a cover plate, immobilizing the protein to the cover plate at a portion which is brought into contact with the cannel, and joining the cover plate with the channel substrate. Alternatively, a commercially available microchip such as the Fluence Microfluidic Tool kit available from Epigem may be used.

In the present invention, the light absorption of the protein on a substrate is directly measured without labeling the protein with a probe or reporter such as a fluorescent dye. Therefore, the protein is required to be immobilized on the substrate at a high density. The immobilization at a high density is one in which a protein is immobilized in such a manner that the number of the protein molecules per unit area of a substrate is large. The amount of the immobilized molecules is not limited, but is 0.5 nmol or more per one type of protein immobilized on a substrate, i.e., per spot area of 1 cm$^2$. The amount is preferably 1 nmol of more, further more preferably 5 nmol or more; or 0.01 µg/mm$^2$ or more, 0.05 µg/mm$^2$ or more, 0.1 µg/mm$^2$ or more, 0.25 µg/mm$^2$ or more, or 0.5 µg/mm$^2$ or more, preferably 1 µg/mm$^2$ or more. When the amount of an immobilized protein per spot is less than this, it is difficult to directly measure light absorption using a spectrophotometer. Further, the density of an immobilized protein can be identified by the degree of light absorption on the protein array. It is desirable that the density be controlled so that the absorbance at a spot of an immobilized protein is 0.0005 or more, 0.001 or more, 0.002 or more, 0.003 or more, 0.004 or more, 0.005 or more, 0.006 or more, 0.007 or more, 0.008 or more, 0.009 or more, or 0.01 or more. In addition, it is desirable that the density be controlled so that a change in absorbance when an immobilized protein is bound to another protein or a compound other than proteins is 0.0005 or more, 0.001 or more, 0.002 or more, 0.003 or more, 0.004 or more, 0.005 or more, 0.006 or more, 0.007 or more, 0.008 or more, 0.009 or more, or 0.01 or more. The area of a spot where a protein is immobilized is not limited, but is from approximately one tenth square millimeters up to ten and several square millimeters, for example, from approximately 1 mm$^2$ up to about 10 mm$^2$. In addition, it will be described later how to determine the absorbance at a spot where a protein is immobilized.

In order to immobilize a protein on a substrate at a high density, it is desirable to immobilize the protein on the substrate with controlled orientation. The immobilization of a protein with controlled orientation is one in which a protein is immobilized on a substrate at one end of the peptide chain of the protein. For example, a protein is immobilized using the carboxy-terminus or amino-terminus of the peptide chain. Examples of a method for immobilizing a protein with controlled orientation are disclosed in JP Patent Nos. 2517861, 2990271, and 3047029 and JP Patent Publication (Kokai) No. 2003-344396A.

For example, a protein represented by the formula $NH_2$—$R_1$—$COOH$ is modified by introducing an amino acid sequence having a cysteine residue at the carboxy-terminus thereof and consisting of several amino acid residues to the carboxy-terminus side of the protein, and then the modified protein is bound to an immobilization substrate via a mercapto group of the cysteine residue at the carboxy-terminus. In this case, the immobilized protein is represented by $NH_2$—$R_1$—$CO$—$NH$—$R_2$—$CO$—$NH$—$Y$ (wherein, $R_1$ and $R_2$ each denote an optional amino acid sequence, and Y denotes an immobilization substrate having a primary amine as a functional group).

For example, the immobilization of a protein can be performed as follows:

A protein array in which a protein $R_1$ is adsorbed on a substrate as shown by the formula $NH_2$—$R_1$—CONH—$R_2$—CO—NH—CH(CH$_2$—SH)—CO—NH—$R_3$—COOH (−)-(+)-$NH_2$—Y (where (−)-(+) represents a state in which binding is formed by adsorption due to ionic attraction) can be prepared by arraying a protein having a sulfide group, which is represented by formula (1) $NH_2$—$R_1$—CONH—$R_2$—CO—NH—CH(CH$_2$—SH)—CO—NH—$R_3$—COOH, on a substrate represented by formula (2) $NH_2$—Y under neutral to weakly alkaline conditions (pH 7 to 10). Furthermore, a protein array in which a protein $R_1$ is immobilized in aligned position on a substrate by a covalent bond, which is shown by the formula $NH_2$—$R_1$—CO—NH—$R_2$—CO—NH—Y, can be obtained by treating the adsorbed protein represented by the aforementioned formula with a cyanating reagent. In the above-mentioned formula, $R_1$ and $R_2$ each denote an optional amino acid sequence, and $R_3$ denotes a chain of amino acid residues which is highly negatively charged at near neutral pH and is capable of adjusting the isoelectric point of a substance represented by formula (1) $NH_2$—$R_1$—CO—NH—$R_2$—CO—NH—CH(CH$_2$—SH)—CO—NH—$R_3$—COOH to be acidic. $R_2$ works as a linker peptide between a protein to be immobilized and represented by the formula $NH_2$—$R_1$—COOH and a substrate. $R_2$ is optionally determined and the type and the number of amino acids thereof are not limited, and an example of which is Gly-Gly-Gly-Gly (SEQ ID NO: 7). $R_3$ is preferably a sequence containing a large number of aspartic acid or glutamic acid. The isoelectric point of a protein depends on the type and the number of amino acids constituting the protein. For example, when a protein contains a large number of basic amino acids such as lysine and arginine, the number of aspartic acid and glutamic acid should be greater than the total number of basic amino acids. It is easy for those skilled in the art to estimate the isoelectric point of a protein by calculation. Preferably, a substance represented by the aforementioned formula (1) may be designed to be a sequence containing a large number of aspartic acid and glutamic acid so that the isoelectric point is between 4 and 5. Among such sequences, alanyl-polyaspartic acid is a preferable sequence. This is because that amide bond-forming reaction readily occurs via a cyanocysteine residue by substituting the amino acid subsequent to cyanocysteine with alanine and that the carboxy group of aspartic acid is the most acidic among side chains of amino acids. Any solution can be used for adsorption reaction as long as the solution is a solvent which can assure the electrostatic interaction and dissolve the protein represented by formula (1) and the pH of the solvent can be controlled. Examples of the solution include dimethylformamide and dimethyl sulfoxide as well as various buffers such as a phosphate buffer and a borate buffer and alcohols such as methanol and ethanol. Though high reaction efficiency can be yielded at room temperature, any temperature range may be adopted without causing difficulties in the range that the solvent used is not frozen or boiled and the protein represented by formula (1) does not aggregate as a result of denaturation. Cyanation reaction can be performed using a cyanating reagent. Generally, it is a simple method to use 2-nitro-5-thiocyanobennzoic acid (NTCB) (see Y. Degani, A. Ptchornik, Biochemistry, 13, 1-11 (1974)) or 1-cyano-4-dimethylaminopyridinium tetrafluoroborate (CDAP) as a cyanating reagent. Commercially available NTCB or CDAP can be used without modification. Cyanation using NTCB can be efficiently carried out at a pH of 7 to 9, and the reaction efficiency can be investigated based on an increase in the absorbance of free thionitrobenzoic acid at 412 nm (the molecular extinction coefficient=13,600 $M^{-1}$ $cm^{-1}$). Cyanation of an SH group can be also carried out in accordance with the process described in the literature (see J. Wood & Catsipoolas, J. Biol. Chem. 233, 2887 (1963)). Cyanation using a cyanating reagent may be carried out after the adsorptive immobilization of a protein represented by formula (1) $NH_2$—$R_1$—CO—NH—$R_2$—CO—NH—CH(CH$_2$—SH)—CO—NH—$R_3$—COOH on an immobilization substrate. Alternatively, it may be carried out simultaneously with the adsorptive immobilization. In the case of the latter, a protein represented by formula (1) and a cyanating reagent may be simultaneously applied to an immobilization substrate. Cyanation treatment can be carried out by the addition of a cyanating reagent to the surface of a substrate having a protein adsorbed thereon. Alternatively, cyanation can be performed by, for example, immersing a whole substrate having a protein adsorbed thereon in a cyanating reagent. Further, a protein is adsorbed on a substrate by the aforementioned arraying means, and then a cyanating reagent may be applied to the substrate at the portion having the protein adsorbed thereon by a similar arraying means. For example, a protein is arrayed and adsorbed on a substrate with a certain dot pattern using a pin, and then a cyanating reagent solution instead of the protein is spotted on the adsorbed protein using a pin. This causes cyanation reaction, and the protein is thereby immobilized. Alternatively, a protein represented by formula (1) $NH_2$—$R_1$—CO—NH—$R_2$—CO—NH—CH(CH$_2$—SH)—CO—NH—$R_3$—COOH and a cyanating reagent may be simultaneously applied to an immobilization substrate.

The immobilization of a protein according to the present invention can be carried out using a spotter (arraying machine). The spotter is an apparatus for transferring a protein sample from a container, such as a microtiter plate, containing the protein sample to a substrate surface by moving a pin tip of a pin for spotting the protein sample or the substrate in the XYZ axes directions with a high performance motor under computer control. Commercially available spotters can be used, and examples of which include SPBIO2000 of Hitachi Software Engineering, GMS417 Arrayer of Takara Shuzo, Gene Tip Stamping of Nippon Laser & Electronics, and Piezo-driven Biochip Spotting System of PerkinElmer.

In addition, a protein array can be fabricated by utilizing ink jet printing technology for the immobilization of a protein according to the present invention. In the protein-immobilizing process according to the present invention, a protein array having an immobilized protein represented by the formula $NH_2$—$R_1$—CO—NH—$R_2$—CO—NH—Y can be fabricated by adsorptively immobilizing a protein represented by formula (1) $NH_2$—$R_1$—CO—NH—$R_2$—CO—NH—CH(CH$_2$—SH)—CO—NH—$R_3$—COOH to an appropriate substrate having an introduced an amino group and represented by $NH_2$—Y by ink jet printing technology, and then cyanating a sulfhydryl group of a cysteine residue of the protein to convert it into a cyanocysteine residue.

Ink jet printers used in printing are classified according to their ink ejection systems. One type is a piezo system using an element (piezo element) which is deformed by the application of voltage, in which an ink storage space in a head is reduced by the deformation of the element, and ink is ejected by this pressure. Another type is a thermal ink jet system, in which a heater in a nozzle is heated to generate foam, and ink is pushed out by this foam. Either type of printer can be used for the immobilization according to the present invention. However, the piezo system printer is preferable when denaturation of proteins by heat is taken into consideration. Commercially available printers can be used as the ink jet printer, and examples of which include ink jet printers of the EPSON PM Series and the Canon PIXUS Series.

An ink cartridge of a printer may be filled with a solution of the protein represented by formula (1) and then may be installed in the printer. Printing patterns of the printer can be freely determined by using appropriate software such as drawing software. A line pattern for immobilizing a protein in the form of a line may be adopted, or a dot pattern for immobilizing a protein as an optional number of dots (spots) in a certain area may be adopted. In addition, the amount of the protein solution discharged in a single discharge can be freely determined. For example, when the line pattern is adopted, a protein may be immobilized in the form of a line with a width of several tens micrometers to several millimeters. The protein can be immobilized with a line pattern having an optional width in such a range by suitably adjusting the amount and the rate of discharge. When the dot pattern is adopted, a protein can be immobilized as circular dots each having a diameter of several micrometers to several millimeters by discharging one drop of the protein solution for every one dot. Alternatively, rectangular dots each having a side of several micrometers to several millimeters can be formed by adjusting the patterning at the time of printing. In this case, the amount and the rate of discharge of the protein solution may be suitably determined depending on a desired dot pattern. In addition, the amount of a protein immobilized in the form of a dot or line is as shown above, and the concentration of the protein solution to be used is desirably about 1 mM to 1 M, the amount of the protein solution to be used for immobilization is desirably about 0.1 µL to 100 µL. However, the concentration and the amount of the protein solution are not limited and optionally changed depending on the amount of the protein to be immobilized.

The number of kinds of proteins to be immobilized or the number of the spots on a single substrate is at least one, preferably 5 or more, more preferably 10 or more, further more preferably 50 or more, and particularly preferably 100 or more.

As described above, when a protein is immobilized on a substrate, an amino group is introduced to the substrate, and the amino group is bound to the carboxy-terminus of a peptide of the protein. In order to introduce an amino group to a substrate, for example, it is necessary to bind a matrix made of a polymer of primary amine having an amino group to the substrate. Examples of the polymer of a primary amine include polyamine, allylamine, and polylysine. Any one of these polymers of a primary amine is mixed with an appropriate carrier, and the mixture is cast on a substrate to form a membrane on the substrate. As the carrier, for example, hydrogel can be used. The term "hydrogel" refers to a gel containing at least a bridge or network structure formed of a polymer and water (as a dispersion liquid) supported or held in the structure. Examples of a water-soluble or hydrophilic polymer compound which provides hydrogel include methyl cellulose, dextran, polyethylene oxide, polypropylene oxide, polyvinyl alcohol, poly-N-vinyl pyrrolidone, poly-N-vinyl acetoamide, polyvinyl pyridine, polyacrylamide, polymethacrylamide, poly-N-methyl acrylamide, polyhydroxymethyl acrylate, polyacrylic acid, polymethacrylic acid, polyvinylsulfonic acid, polystyrenesulfonic acid, and salts thereof, poly-N,N-dimethylaminoethylmethacrylate, poly-N,N-diethylaminoethylmethacrylate, poly-N,N-dimethylaminopropylacrylamide, and salts thereof. In addition, a commercially available carrier containing a primary amino group, such as Amino-cellulofine (available from Seikagaku Kogyo), AF-Amino Toyopearl (available from TOSOH), EAH-Sepharose 4B or lysine-Sepharose 4B (available from Amersham Pharmacia), Affigel 102 (available from BioRad), or Porous 20 NH (available from Boehringer Mannheim), may be used. In this process, binding of a polymer of a primary amine and a carrier such as polyacrylamide requires polymerization of the carrier, and ultraviolet irradiation is effective, for example.

The binding of a matrix and a substrate such as glass may be carried out, for example, using a silane coupling agent. The silane coupling agent is a material which can form covalent bonds with a glass surface and the matrix such as polyacrylamide and thereby provide a binding between an organic material and an inorganic material. Generally, a silane coupling agent is a compound having a structure of R—Si—$X_3$, wherein X is an alkoxy group such as a methoxy group (—$OCH_3$). This alkoxy group is converted into a silanol group (Si—OH) by hydrolysis. This silanol group reacts with a silanol group present on the substrate surface to form a hydrogen bond or a stable siloxane bond (Si—O—Si) by reaction such as dehydrated condensation. Thus, a coat of a hydrophobic group R— is formed on the substrate surface. At the same time, R— is an organic functional group (for example, $H_2C$=$C(CH_3)C$(=O)O—$(CH_2)_3$—) which is capable of binding to the matrix. Commercially available silane coupling agents such as Bind-silane (3-methacryloxypropyltrimethoxysilane) available from Amersham can be used.

The protein immobilized on a substrate is irradiated with light, and the light absorption of the protein is measured. Preferably, the protein immobilized on an ultraviolet light-transmissive substrate is irradiated with ultraviolet light, and the ultraviolet light absorption of the protein is measured. The light-irradiating means may be a spectroscope. Examples of the spectroscope include a spectroscope utilizing an optical filter, a dispersive spectroscope, and a Fourier transform spectroscope. When ultraviolet light is irradiated, a dispersive spectroscope is desirable. The light used may be any one of ultraviolet light, visible light, and infrared light. When ultraviolet light is used, the wavelength is 200 to 310 nm. When a protein is measured, the wavelength of ultraviolet light is desirably about 280 nm, about 224 to 236 nm, or about 205 nm, which are absorbed by proteins. When a compound other than proteins is measured, light having a wavelength which is specifically absorbed by the compound may be used. The wavelength of light irradiated may be fixed at a constant one. Alternatively, the measurement may be carried out using a plurality of fixed wavelengths of light or while changing the wavelength. By changing the wavelength when the measurement is carried out, the absorption spectrum of a protein on a protein array or a compound other than proteins and has interacted with the protein can be obtained. For example, the measurement can be carried out using a commercially available spectrophotometer by mounting a substrate on which a protein is immobilized according to the present invention on a cell chamber where a cell of the spectrophotometer is mounted on. The surface to which the protein is immobilized may face toward the light-irradiating means side or, contrarily, the light-detecting means side. In addition, an appropriate portion of the substrate can be irradiated with light by controlling the width of the optical path or the like by providing a lens and a slit on the optical path to the substrate from the light-irradiating means irradiating the light toward the substrate.

Further, when a two-dimensional photodetector such as a CCD is used, the light transmitted through the individual spot can be measured at once by irradiating the whole immobilized protein spotted on the substrate with light. When a one-dimensional photodetector is used, all spots may be irradiated with light by moving the light-irradiating means so that only a certain spot on the substrate is irradiated with light at a time. In this case, the photodetector is moved synchronously with the movement of the light-irradiating means.

When a protein-immobilized substrate is irradiated with light, the light is absorbed by the immobilized protein, a protein bound to the immobilized protein, and/or a compound which is other than proteins and bound to the immobilized protein. In the present invention, the light transmitted the substrate without being absorbed is measured. The measurement of the transmitted light is carried out by using a light-detecting means. The light-detecting means outputs the light intensity as an electric signal and may be either photodetector employing internal photoelectric effect or external photoelectric effect. The photodetector employing internal photoelectric effect is one in which charge separation caused by light in a semiconductor material is used, and there are a photoconductive photodetector which detects a change in the electrical conductivity of a carrier due to the charge separation and a photovoltaic photodetector which detects a potential difference. Examples of the photoconductive photodetector are a charge coupled device (CCD), a photodiode (PD), and a photodiode array (PDA). The photodetector employing external photoelectric effect is one in which electrons are discharged into a vacuum from a photoelectric surface by incident photons and the electrons are detected directly or after amplification, and examples of which are a photoelectric tube and a photomultiplier.

In the unit according to the present invention, though any of the aforementioned light-detecting means can be adopted, a PDA or a CCD, which is a multi-channel detector, is desirable; and a CCD, which is a two-dimensional multi-channel detector, is further desirable. In addition, the PDA and CCD can be used as an IPDA or an ICCD by attaching an electron-multiplying function thereto with a microchannel plate. In the present invention, such IPDA and ICCD are included in the PDA and the CCD, respectively.

When ultraviolet light is used as the irradiation light and the transmitted ultraviolet light is measured, the CCD must be ultraviolet light-responsive. Examples of the ultraviolet light-responsive CCD include IMPACTRON™ CCD elements such as TC253SPD-30/TC253SPD-B0 and TC285SPD-30/TC285SPD-B0 available from Texas Instruments and CCD elements available from HORIBA Jobin Yvon. In addition, commercially available CCD cameras using these elements may be used. Examples of such cameras include IMPACTRON™ CCD digital cameras such as MC681SPD and MC285SPD-L0B0 available from Texas Instruments. However, ultraviolet light-responsive cameras have a problem that they are extremely expensive. A CCD not responsive to ultraviolet light, which is employed in readily commercially available CCD cameras, can be used by adopting an ultraviolet-visible light converting device. The ultraviolet-visible converting device is a nonlinear optical material and converts ultraviolet light into visible light. Examples of the device include wavelength converting glass such as fluorescent glass, a fluorescent material such as a fluorescent pigment, and a sensitizer such as a silver halide sensitizer and a non-silver halide sensitizer. Among them, fluorescent glass is desirable. The fluorescent glass is one in which a rare-earth ion serving as a fluorescent active ion is contained in glass and converts irradiated ultraviolet light with a wavelength of 200 to 400 nm into visible light with a wavelength of 400 nm or more. Examples of the fluorescent glass include Lumilass-G9, Lumilass-R7, and Lumilass-B available from Sumita Optical Glass, which emit green fluorescent light of wavelength 540 nm, red fluorescent light of wavelength 610 nm, and blue fluorescent light of wavelength 410 nm, respectively, by irradiation of ultraviolet light with a wavelength of 200 to 400 nm. In the unit according to the present invention, the fluorescent glass may be placed between an ultraviolet light-transmissive substrate on which a protein is immobilized and a light-detecting means. In addition, the fluorescent pigment or the sensitizer may be applied to a glass plate and the glass plate may be placed between an ultraviolet light-transmissive substrate on which a protein is immobilized and a light-detecting means. Alternatively, the fluorescent pigment or the sensitizer may be applied to an ultraviolet light-transmissive substrate at the side not immobilizing a protein. In the latter case, the face immobilizing a protein is irradiated with ultraviolet light.

As described above, an ultraviolet light transmissive substrate on which a protein is immobilized is irradiated with ultraviolet light, and the ultraviolet light not absorbed by the immobilized protein or the visible light converted from the ultraviolet light is detected by a light-detecting means.

The light-detecting means outputs a signal as image data or video data, and an analyzing means processes the signal to measure the light absorption of the protein on the substrate. The type of the image data is not limited. For example, the image data obtained as a BMP image can be processed. The image data or video data are processed to give the light intensity at each spot on the substrate. The processed data may be displayed by, for example, different colors coding the spots based on the absorption difference or three-dimensional coordinates showing the absorbance by height according to the two-dimensional coordinates of the substrate.

The video data are obtained by taking images of the protein-immobilizing substrate with a video camera having a CCD. The video data allow analyzing the light absorption of the protein on the substrate in real time. Video data can be processed in real time by using a video capture board or commercially available software such as Direct X (available from Windows).

On this occasion, the intensity of light transmitted the substrate at a portion where proteins are not immobilized and the intensity of light transmitted the substrate at a portion where a protein is immobilized are measured. The transmittance of the portion where a protein is immobilized is calculated using the transmittance of the portion where proteins are not immobilized as 100%. The data given by the light-detecting means are expressed as pixels. An average light intensity ($I_0$) of a plurality of pixels at an optional portion where proteins are not immobilized is determined, and an average light intensity of a plurality of pixels at each portion (spot or dot) where a protein is immobilized is also determined. The optical transmittance (I) at each spot can be determined from these average light intensities. The absorbance can be determined from $-\log(I/I_0)$. On this occasion, the immobilization density of an immobilized protein to be measured can be determined based on the relationship between the immobilization density and the absorbance, which is determined in advance using a standard protein of which immobilization density or protein mass in one spot is known. For example, when the absorbance of a standard protein having a density of D is As and the absorbance of a tested protein of which density is not known is At, the density of the tested protein can be calculated according to an expression D×(At/As). In addition, the standard protein with a known density may be immobilized on a substrate as a control spot.

The wavelength of ultraviolet light irradiated to a protein-immobilizing substrate by a light-irradiating means may be fixed at a constant one. Alternatively, wavelength scan may be performed at intervals of one to several tens nanometers.

An immobilized protein is brought into contact for reaction with another protein which interacts with the immobilized protein or a compound other than proteins, such as a low molecular compound, and then the light absorption at a spot on the substrate can be measured. For example, the interaction between an immobilized protein and a ligand protein which binds to the immobilized protein can be detected/analyzed. In addition, the interaction between an immobilized protein and a ligand other than proteins can be detected/analyzed. For example, the amount of an antigen or antibody bound to an immobilized antibody or antigen can be measured by immobilizing the antibody or antigen on a substrate at a certain density, reacting the antigen or antibody which specifically binds to the immobilized antibody or antigen, and measuring absorption of the protein on the substrate. In this case, when the light absorption of the protein array is measured before and after the contact for reaction of the immobilized protein with another protein or a compound other than proteins, the measurement value before the contact is based on the light absorption of the immobilized protein alone and the measurement value after the contact is based on the light absorption of a complex formed by the interaction between the immobilized protein and the another protein or the compound other than proteins. Therefore, the amount of the protein or the compound other than proteins, which has interacted with the immobilized protein, can be determined by the difference in the light absorption before and after the contact. The interaction of an immobilized protein on a substrate with another protein and the amount of the interacted another protein can be measured by obtaining the absorption of the immobilized protein on the substrate in advance, bringing the another protein into interaction, then measuring the absorption again, and determining the change in the absorption before and after the interaction. On this occasion, only a protein compound which has interacted with the immobilized protein can be specifically measured by using light having a wavelength which is specifically absorbed by the compound which interacts with the immobilized protein. Further, changes in the light absorption on a protein array during the contact can be measured in real time over before and after the contact by using a flow cell or a microchip having a channel for liquid as the substrate and forming a flow unit. Therefore, the interaction over time can be monitored.

Furthermore, in the measurement of the binding of a low molecular ligand to an immobilized protein, a change in the ultraviolet absorption based on the absorption of an aromatic amino acid side chain accompanied with the binding of the ligand can be used. For example, the association constant, which is an indicator of the strength of binding of the ligand, can be determined by changing the concentration of a ligand which does not absorb ultraviolet and measuring a change in the ultraviolet absorbance at a specific wavelength or a change in the ultraviolet absorption spectrum, accompanied with the binding of the ligand. In addition, since many proteins do not absorb visible light, in a ligand which exhibits a visible absorption, the association constant, which is an indicator of the binding or the strength of the binding concerning the ligand, can be determined by measuring a change in the visible absorption at a specific wavelength or a change in the visible absorption spectrum.

EXAMPLES

The present invention will be specifically described with reference to the following examples, but the present invention is not limited by these examples.

In this example, a base material for a protein array was prepared by forming a thin sheet of a polyacrylamide gel containing a polymer having an amino group on a surface of quartz glass. Since this base material substantially did not absorb light in the wavelength range of visible light and ultraviolet light (transparent), the optical activity of a protein present in the gel was able to be directly detected. In other words, an immobilized protein and a protein which interacted with the immobilized protein were able to be detected/analyzed by an optical method, without a specific labeling process.

In this example, a green fluorescent protein (SEQ ID No:1) and dihydrofolate reductase (SEQ ID NO:4) were immobilized on this base material for a protein array. Since the green fluorescent protein was green under natural light and was able to be readily confirmed by the naked eye, it was used for monitoring the immobilization process. On the other hand, since dihydrofolate reductase had a property, as in general proteins, absorbing ultraviolet light at wavelength around 280 nm, it was used as a test protein for detecting the optical activity on the array after the immobilization.

Hereinafter, [1] a fabrication process of a base material for a protein array, [2] preparation of a green fluorescent protein for immobilization, [3] preparation of dihydrofolate reductase for immobilization, [4] adsorption and alignment of a protein to the base material for the array, [5] immobilization of the adsorbed protein, and [6] measurement of an optical activity of the protein immobilized on the array will be specifically described.

[1] Fabrication of Base Material for Protein Array

In the fabrication of a base material for an array, first, bind-silane was applied to a surface of quartz glass (processed into a slide glass having a size of 7.7 cm×2.6 cm×1 mm, VIOSIL-SG2AS purchased from Shin-Etsu Chemical), and then a thin sheet (2.4 cm×5.0 cm× about 50 μm) of a polyacrylamide gel containing a polymer (poly-L-lysine having a molecular weight of 30000 to 70000 purchased from Sigma) having an amino group was formed.

Since bind-silane (purchased from Amersham) had a property of forming a covalent band with both quartz slide glass and polyacrylamide molecules, it was used for tightly binding the both. Specifically, bind-silane was applied to a surface of a quartz slide glass as follows: a solution was prepared by mixing 8 mL of ethanol, 0.2 mL of acetic acid, 1.8 mL of pure water, and 10 μL of bind-silane. The solution (0.5 mL) was dropwise applied to a quartz slide glass, was spread to the entire surface with a kimwipe, and was dried for 1.5 hrs.

Then, a thin sheet of a polyacrylamide gel was formed, as described below, on the surface of the quartz slide glass to which bind-silane was thus applied. First, a 12.5% polyacrylamide solution was prepared by dissolving a mixture of acrylamide and methylene-bis-acrylamide (37.5:1) (purchased from BioRad) into pure water. To this solution, poly-L-lysine (poly-L-lysine having a molecular weight of 30000 to 70000 purchased from Sigma) and pure water were added on ice to prepare 1 mL of a solution of which final concentration of polyacrylamide was 10% and that of poly-L-lysine was 0.5%. Then, 1 μL of TEMED (purchased from BioRad), which was a gelling (solidifying) agent for polyacrylamide, and 7.5 μL of a 10% ammonium persulfate solution (purchased from Nacalai) were added to the solution, and the resulting mixture was well mixed. Then, 0.3 mL of this solution was dropwise applied to the bind-silane-applied quartz slide glass. Then, immediately, a gap cover glass (purchased from Matsunami glass) was covered over the slide glass so that air bubbles did not enter. In the above-described process, for avoiding the progress of involuntary gelling, the preparation of solutions was carried out on ice and the process should be performed as rapid as possible. Subsequently, the slide glass was left standing overnight at room temperature for gelling polyacrylamide. After the completion of the gelling, the slide glass was irradiated with ultraviolet light (360 nm) using a transilluminator (purchased from UVP) for 5 min, and then the whole quartz slide glass was immersed in pure water in a Petri dish and stirred for 30 min. The slide glass was taken out from the Petri dish, and the gap cover glass was removed with a pair of tweezers. Then, the slide glass was immersed in pure water in a Petri dish again and stirred overnight, then further washed with pure water twice, and dried for several hours.

[2] Preparation of Green Fluorescent Protein for Immobilization

A protein (SEQ ID NO:3) corresponding to formula (1) $NH_2—R_1—CO—NH—R_2—CO—NH—CH(CH_2—SH)—CO—NH—R_3—COOH$ was prepared as an immobilization protein by adding a sequence consisting of Gly-Gly-Gly-Gly-Gly-Gly-Cys-Ala-Asp-Asp-Asp-Asp-Asp-Asp (SEQ ID NO:2), as a sequence for immobilization, to the carboxy-terminus of a green fluorescent protein (GFP) (SEQ ID NO:1). Conditions for immobilization reaction were investigated using this protein.

A recombinant plasmid was constructed by synthesizing a DNA sequence containing a DNA sequence encoding SEQ ID NO:2, a ribosome binding sequence necessary for gene expression, and a restriction enzyme cleavage site necessary for insertion into a vector and inserting the resulting DNA sequence between EcoRI and HindIII of expression vector pUC18. This plasmid was introduced into *E. coli* strain JM109. The expression and sequential isolation and purification were carried out as follows:

The recombinant *E. coli* expressing the green fluorescent protein for immobilization was cultured in two liters of a medium (containing 10 g of sodium chloride, 10 g of yeast extract, 16 g of tryptone, and 280 mg of sodium ampicillin) at 37° C. overnight. The culture medium was centrifuged at a low speed (5000 rpm) for 20 min to obtain approximately 5 g wet weight of bacterial cells. The bacterial cells were suspended in 30 mL of a 10 mM phosphate buffer solution (pH 7.0) containing 1 mM ethylene diamine tetra-acetate (EDTA) and were disrupted with a French press to obtain a cell-free extract. The obtained protein was purified to a homogeneous state by being subjected to streptomycin sulfate treatment, ammonium sulfate treatment, purification by DEAE-Toyopearl chromatography (purchased from Tosoh), and purification by SuperQ Toyopearl chromatography (purchased from Tosoh). Thus, approximately 60 mg of homogenous green fluorescent protein for immobilization was obtained. The concentration of the green fluorescent protein for immobilization was determined from the absorbance at 280 nm based on the molecular extinction coefficient, 22000 $M^{-1} cm^{-1}$, of the green fluorescent protein. In addition, the green fluorescent protein for immobilization shown by SEQ ID NO:3 can be readily produced by those skilled in the art if a gene encoding the green fluorescent protein shown by SEQ ID NO:1 is available.

[3] Preparation of Dihydrofolate Reductase for Immobilization

A protein (SEQ ID NO:5) corresponding to formula (1) $NH_2—R_1—CO—NH—R_2—CO—NH—CH(CH_2—SH)—CO—NH—R_3—COOH$ was prepared as an immobilization protein by adding a sequence consisting of Gly-Gly-Gly-Gly-Cys-Ala-Asp-Asp-Asp-Asp (SEQ ID NO:6), as a sequence for immobilization, to the carboxy-terminus of a mutation of a dihydrofolate reductase (abbreviated as AS-DHFR) (SEQ ID NO:4). The optical activity of the protein at the ultraviolet region was detected on an array.

A recombinant plasmid was constructed by synthesizing a DNA sequence containing a DNA sequence encoding SEQ ID NO:5, a ribosome binding sequence necessary for gene expression, and a restriction enzyme cleavage site necessary for insertion into a vector and inserting the resulting DNA sequence between EcoRI and HindIII of expression vector pUC18. This plasmid was introduced into *E. coli* strain JM109. The expression and sequential isolation and purification were carried out as follows:

The recombinant *E. coli* expressing the AS-DHFR for immobilization was cultured in two liters of a medium (containing 10 g of sodium chloride, 10 g of yeast extract, 16 g of tryptone, and 280 mg of sodium ampicillin) at 37° C. overnight. The culture medium was centrifuged at a low speed (5000 rpm) for 20 min to obtain approximately 5 g wet weight of bacterial cells. The bacterial cells were suspended in 30 mL of a 10 mM phosphate buffer solution (pH 7.0) containing 1 mM ethylene diamine tetra-acetate (EDTA) and were disrupted with a French press to obtain a cell-free extract. The obtained protein was purified to a homogeneous state by being subjected to streptomycin sulfate treatment, ammonium sulfate treatment, purification by methotrexate affinity chromatography (purchased from Sigma), and purification by DEAE-Toyopearl chromatography (purchased from Tosoh). Thus, approximately 70 mg of the AS-DHFR for immobilization was obtained. The concentration of the AS-DHFR for immobilization was determined from the absorbance at 280 nm based on the molecular extinction coefficient, 31100 $M \cdot cm^{-1}$, of the AS-DHFR. In addition, the AS-DHFR for immobilization shown by SEQ ID NO:5 can be readily produced by those skilled in the art if a gene encoding the protein shown by SEQ ID NO:4 is available.

[4] Adsorption and Alignment of Protein to Base Material for Array

The green fluorescent protein for immobilization or the AS-DHFR for immobilization was adsorbed and aligned on the base material for an array prepared in the above [1] as in below. A pipette tip having an opening with a radius of about 0.5 mm (purchased from QSP) for microloading was attached to a syringe having a capacity of 10 μL (purchased from Hamilton) for microinjection, and the syringe was mounted on a hydraulic controller purchased from Narishige to use as a micromanipulator. The micromanipulator was used as a device for spotting a protein by moving the holder in three directions: vertical, side to side, and front to back. By using this device, the spotting of a protein was able to be controlled at a 0.5 mm level regarding the position and at a 0.1 μL level regarding the amount of the solution.

The spotting of the green fluorescent protein onto a substrate was performed by preparing five concentrations, 2.5 mg/mL, 5 mg/mL, 10 mg/mL, 20 mg/mL, and 40 mg/mL, of the green fluorescent protein solution for immobilization and spotting 0.2 μL of each solution on the array base material from the dilute protein solution in order. That is, 0.2 μL of the 2.5 mg/mL protein solution was spotted at each of three positions with a distance of 5 mm apart from each other in one line in the longitudinal direction on the leftmost of the array substrate. Then, 0.2 μL of the 5 mg/mL protein solution was spotted at each of three positions with a distance of 5 mm from each other in one line in the longitudinal direction on the right side of the line of the 2.5 mg/mL protein solution with a distance of 4 mm therebetween. Similarly, 0.2 μL of each solution of the 10 mg/mL, 20 mg/mL, and 40 mg/mL protein concentrations was spotted. Thus, 0.5 μg, 1 μg, 2 μg, 4 μg, and 8 μg of green fluorescent protein were each spotted at each of three positions. The protein solutions were formed into liquid droplets with a diameter of approximately 1 mm on the surface of the gel immediately after the spotting and then rapidly absorbed into the inside of the gel. After the completion of the spotting, the whole array base material was immersed in a 10 mM phosphate buffer solution (pH 7.0), and then the appearances of the spots were observed. In the spots of 0.5 µg, 1 µg, and 2 µg of the protein, diffusion of the spot was not observed, but in 4 µg and 8 µg of the protein, it was observed that the fluorescent protein was gradually diffused into the buffer solution. Thus, it was observed that the amount of the protein adsorbed in the substrate was the same as that when 2 µg of the protein was spotted, even if the more than 2 µg of the protein was spotted. This means that the upper limit of the surface density of the adsorbable fluorescent protein is about 2.5 µg/mm$^2$, from the fact that the diameter of a spot is about 1 mm. In addition, the adsorbed green fluorescent protein was detached from the gel thin sheet by sufficiently washing the array base material with 1 M of KCl before the immobilization reaction shown in [5] below.

The AS-DHFR for immobilization was similarly adsorbed to an array base material.

[5] Immobilization Reaction

Figure 3:
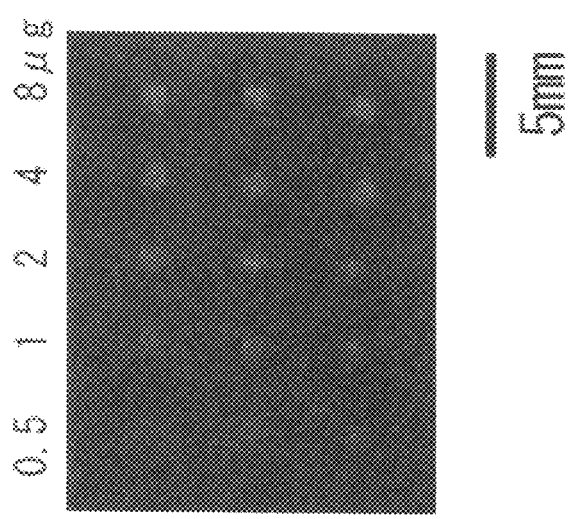
FIG. 3 is a photograph of a green fluorescent protein-immobilizing base material for a protein array taken under natural light.

The whole substrate adsorbing the green fluorescent protein for immobilization or the AS-DHFR for immobilization prepared in the above [4] was moisturized with 1 mL of a 10 mM phosphate buffer solution (pH 7.0) containing 5 mM of 2-nitro-5-thiocyanobenzoic acid (NTCB) and left standing at room temperature for 4 hr for cyanation reaction of the protein. Then, the substrate was sufficiently washed with a 10 mM phosphate buffer solution (pH 7.0), and the excessive reagent and so forth were removed. Then, the substrate was immersed in a 10 mM borate buffer solution (pH 9.5) and gently stirred at room temperature for 24 hr for immobilization reaction. After the completion of the immobilization reaction, the slide glass was entirely immersed in a 10 mM phosphate buffer solution (pH 7.0) containing 1 M of KCl in a Petri dish and gently stirred for 24 hr for removing unreacted protein and side reaction products. FIG. 3 shows the results. This is a photograph of a green fluorescent protein-immobilizing array base material taken under natural light. It was suggested from the fluorescence intensity of the immobilized protein that the upper limit of the surface density of the immobilizable fluorescent protein was approximately 2 µg/mm$^2$ when the substrate prepared in this example was used.

[6] Measurement of Optical Activity of Immobilized Protein

The optical activities of the immobilized proteins were measured.

Figure 4:
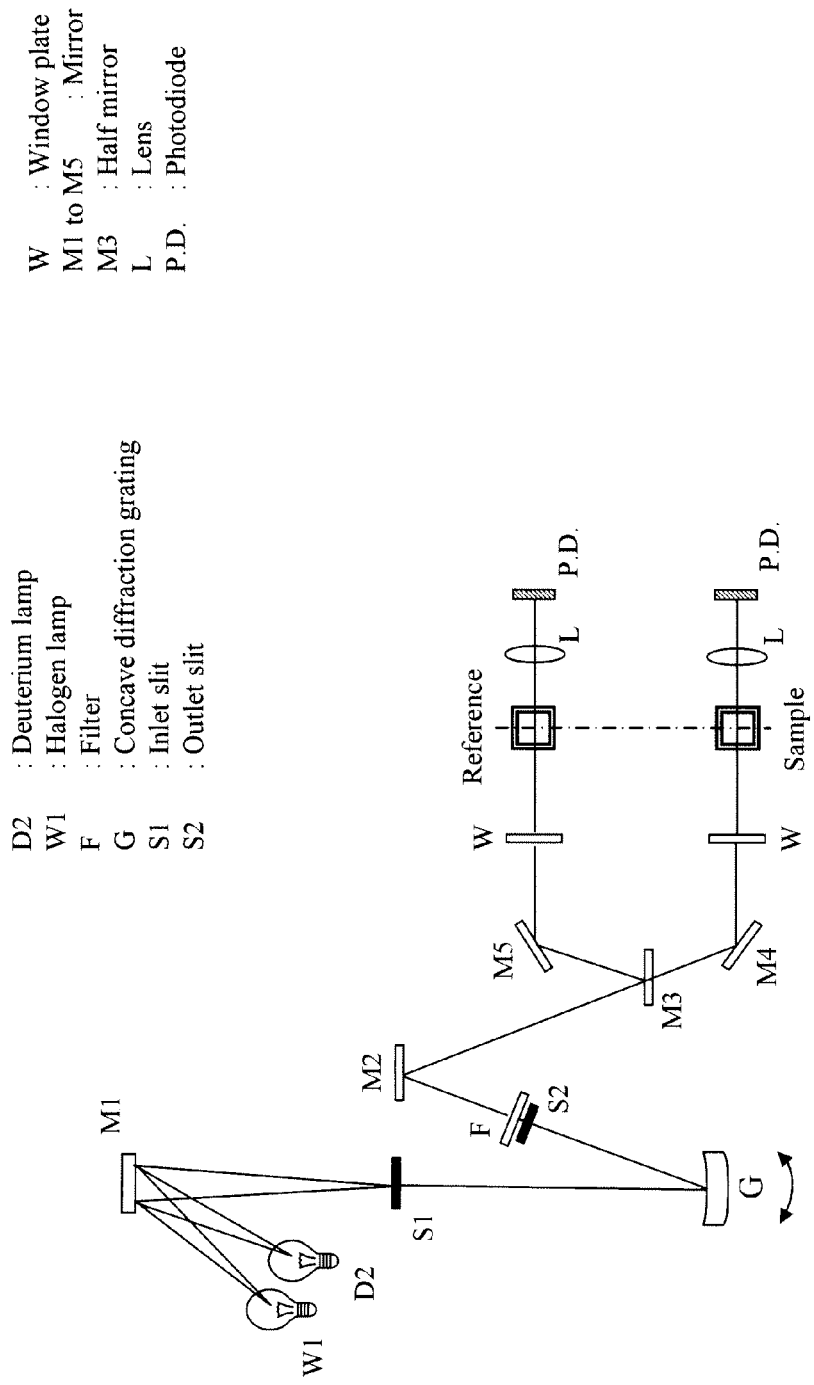
FIG. 4 is an optical system diagram (optical path) of an observation unit used in an example.

The apparatuses used for the measurement were as follows:

Shimadzu UV-1200 or AVIV-ATG14 was used as a light source for light irradiation. The former has characteristics that the slit width cannot be changed and the output is relatively low such as about 30 W (0.3 mA×100 V). In the latter, a xenon lamp (450 W) is employed and the slit width is changeable. The optical path of light from a diffraction grating of such a light source was transferred to the outside using a UV dedicated mirror placed between the diffraction grating and a cell holder, and thus an observation unit was constructed. FIG. 4 is an optical system diagram (optical path) of the observation unit using Shimadzu UV-1200. In the optical system diagram in FIG. 4, since the diffraction grating was disposed in the optical system, the wavelength was adjusted in the system-controlling unit.

Figure 5:
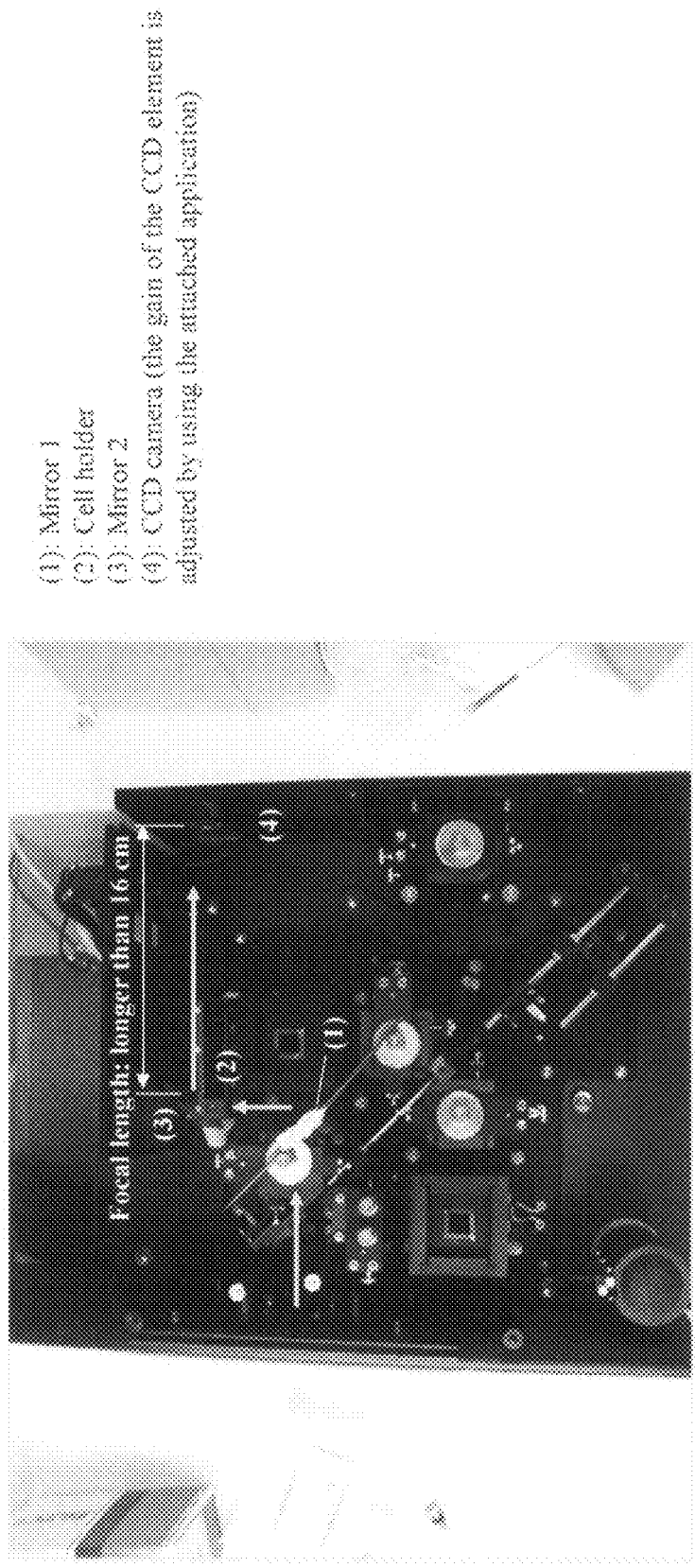
FIG. 5 is an optical system diagram when spectrophotometer AVIV ATF104 is used.
Figure 6:
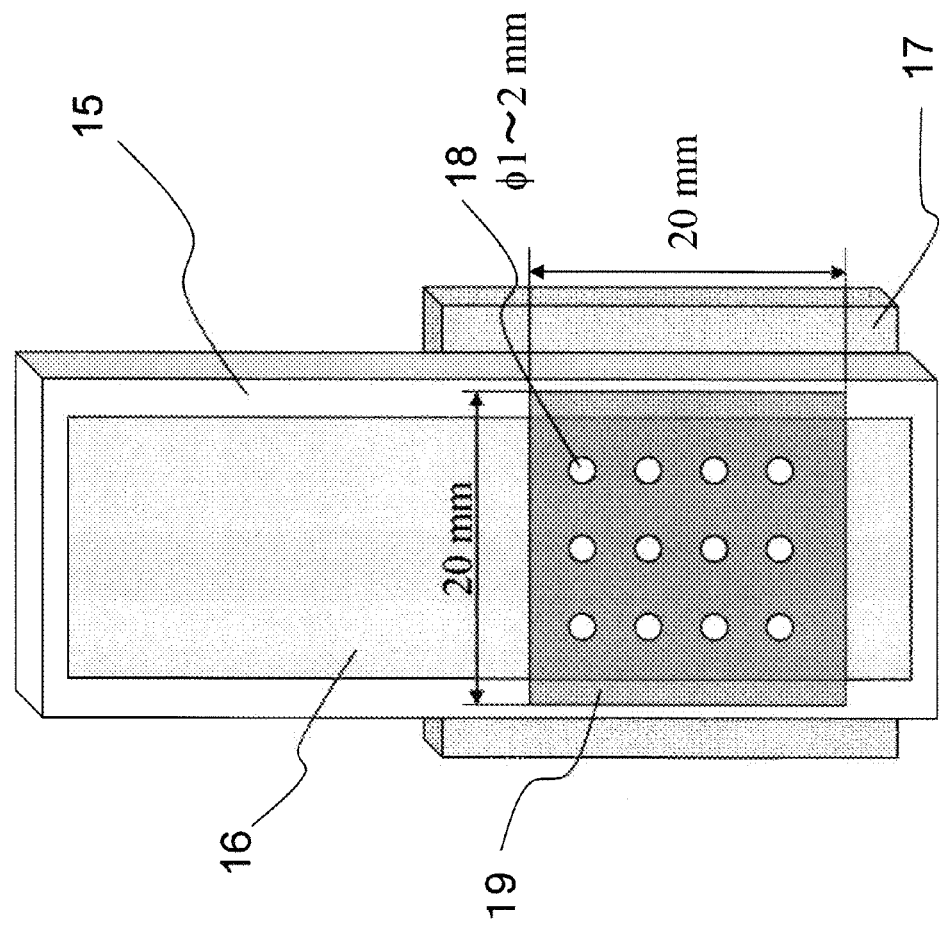
FIG. 6 is a diagram showing a combination of a protein-immobilizing substrate and fluorescent glass.

FIG. 5 is an optical system diagram when the above-mentioned AVIV ATF104 was employed. In the figure, a light source was placed at the left side of the apparatus, and light moved as shown by the arrows. A mirror 1 was placed at the position indicated by numeral 1, a substrate holder (cell holder) was placed at the position indicated by numeral 2, a mirror 2 was placed at the position indicated by numeral 3, and a CCD camera was placed at the position indicated by numeral 4. The CCD camera was togicool Qcam QV-700N available from Logicool and had 300000 pixel resolution. The gain adjustment and the like of the CCD element were performed by an application attached to the CCD camera. The focal length from the mirror placed at the position indicated by numeral 3 in the figure to the CCD camera was controlled to 18 cm or more. The protein-immobilizing substrate mounted on the above-mentioned substrate holder was prepared by immobilizing DHFR spots each having a diameter of 1 to 2 mm within an area of 20×20 mm on a synthetic quartz glass substrate as in the above [1] to [5]. The protein mass per spot was 10, 15, or 20 µg. Lumilass-B available from Sumita Optical Glass was used as the ultraviolet-visible converting device. FIG. 6 is a diagram showing a glass substrate on which AS-DHFR was immobilized. As shown in FIG. 6, the AS-DHFR-immobilizing glass substrate and fluorescent glass were combined. The diameter of each spot was 1 to 2 mm, the light cross section which was irradiated with light had a size of 20×20 mm, and the distance between the spots was less than 4 mm. As shown in the right in FIG. 7, the protein mass immobilized at each spot was 10, 15, and 20 µg/spot from the right column. The image of fluorescence irradiated from the fluorescent glass when ultraviolet light with a wavelength of 280 nm was irradiated was taken. The image was taken under the conditions of a shutter speed of 1/30, the maximum gain, and an image size of 320×240. The image is shown in the left in FIG. 7.

Figure 7:
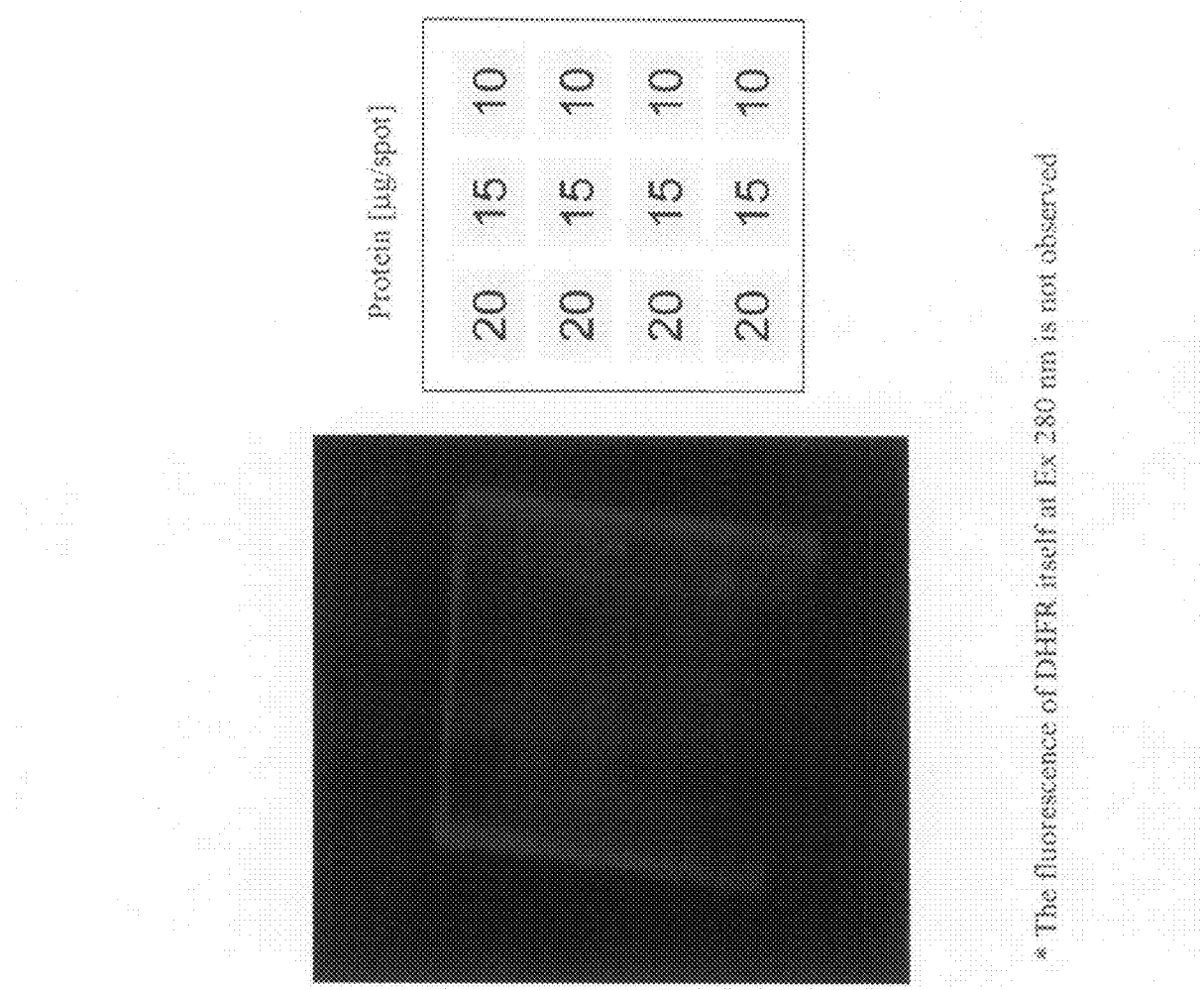
FIG. 7 is a photograph of fluorescence irradiated from fluorescent glass when a DHFR-immobilizing slide glass and fluorescent glass are combined and ultraviolet light having a wavelength of 280 nm is irradiated. The table in the right in FIG. 7 shows the mass of the protein used for each spot.

As shown in FIG. 7, the transmitted ultraviolet light at the spots where the DHFR was immobilized was weak because of the ultraviolet light absorption of the immobilized DHFR, and therefore fluorescence was not emitted from the fluorescent glass. Consequently, only the places corresponding to the spots were not luminous. Further, in the above-described conditions, the immobilization density was excessively high, and thereby the absorption was large enough to saturate the absorbance.

Figure 8:
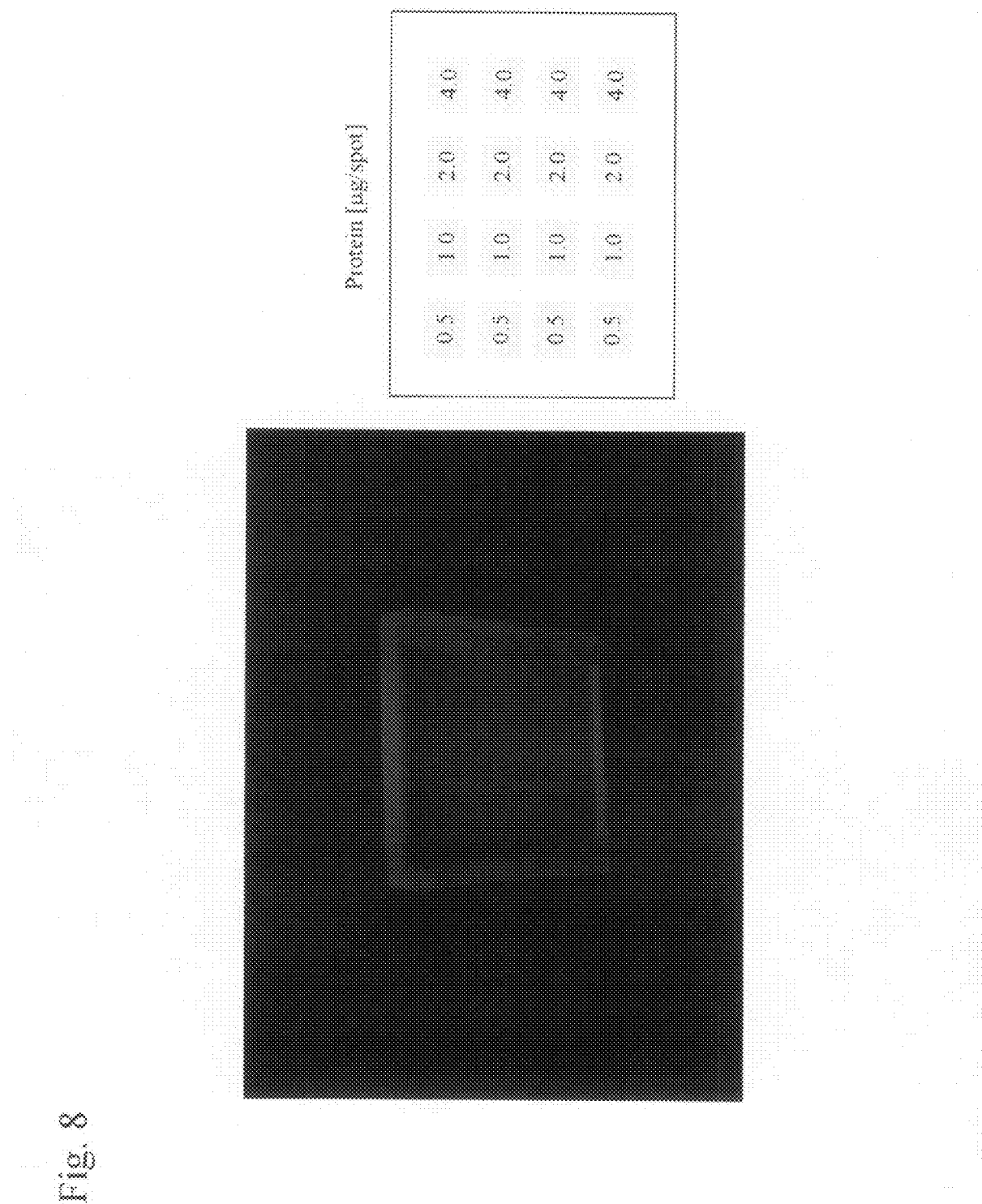
FIG. 8 is a photograph of fluorescence irradiated from fluorescent glass taken with a high-resolution CDD when slide glass-immobilized DHFR at 0.5 to 4 µg/spot and fluorescent glass are combined and ultraviolet light having a wavelength of 280 nm is irradiated. The table in the right in FIG. 8 shows the mass of the protein used for each spot.

In order to perform the measurement at higher immobilization density, the same investigation was carried out using a CCD with higher resolution. The used CCD camera was Coolpix4300 available from Nikon. Images were taken under conditions of a shutter speed of 1/4 and from a distance of 4 cm using the closeup function of the camera. In this occasion, the focal point was manually adjusted. The image size was 640× 480, and the wavelength of the irradiated light was 280 nm. As in the above, the DHFR was spotted on synthetic quartz glass, the glass was combined with fluorescent glass, and then ultraviolet light with a wavelength of 280 nm was irradiated. As shown in the right in FIG. 8, the mass of the spots was adjusted to 0.5, 1, 2, and 4 µg from the right column. The image is shown in the left in FIG. 8.

Figure 9:
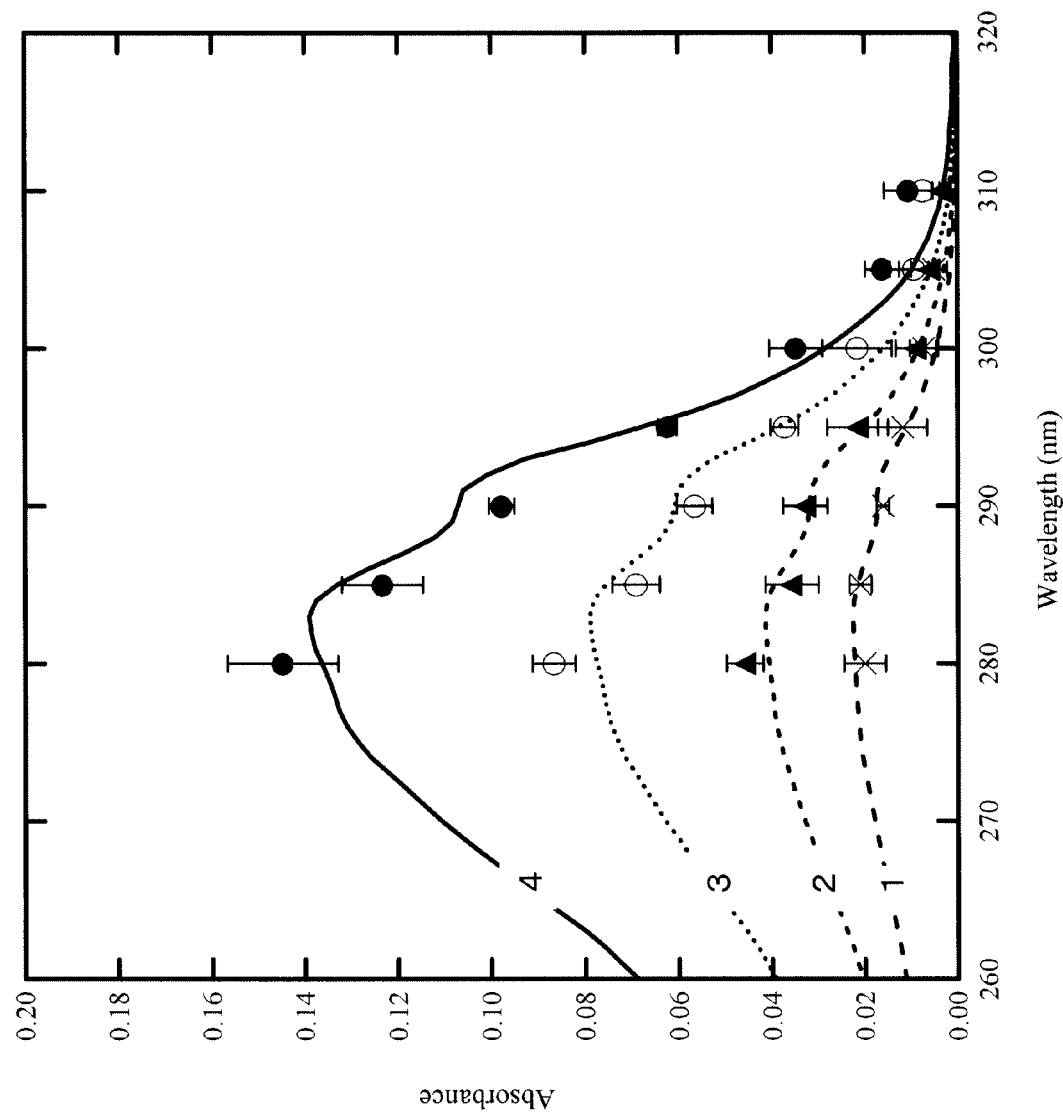
FIG. 9 shows absorbance, i.e., absorption spectra, when each spot is irradiated with ultraviolet light while changing the wavelength in the range from 280 to 310 nm with an increment of 5 nm. In the figure, x, Π, ○, and ● indicate averages (of four spots each) of the spots of 0.5, 1, 2, and 4 µg/spot, respectively, and error bars are drawn for each point. For comparison, spectra of AS-DHFR in solutions with concentrations of 0.7 µM (spectrum shown by a curve 1 in the figure), 1.3 µM (spectrum shown by a curve 2 in the figure), 2.5 µM (spectrum shown by a curve 3 in the figure), and 4.4 µM (spectrum shown by a curve 4 in the figure) are drawn.

This protein-immobilizing substrate was irradiated with ultraviolet light while changing the wavelength in the range from 280 to 310 nm with an increment of 5 nm, and the fluorescence emitted from the fluorescent glass was measured. The absorbance was determined by $\log(I_0/I)$ using the intensity $I_0$ of light emitted from the fluorescent glass at a portion on the substrate where the protein was not spotted and the intensity I of light emitted from the fluorescent glass at a portion where the protein was spotted. The average of absorbance of four spots at each concentration was calculated. FIG. 9 shows the results when the average values and error bars were plotted with respect to the wavelength of irradiated ultraviolet light. The linear density of the protein at each of the spots of 0.5, 1, 2, and 4 µg was estimated from the absorbance at 280 nm to be 0.6 nmol/cm$^2$, 1.5 nmol/cm$^2$, 2.8 nmol/cm$^2$, and 4.7 nmol/cm$^2$, respectively, on the basis of the molecular extinction efficient of the AS-DHFR. Further, it was determined to be 0.7 µM (spectrum shown by a curve 1 in the figure), 1.3 µM (spectrum shown by a curve 2 in the figure), 2.5 µM (spectrum shown by a curve 3 in the figure), and 4.4 µM (spectrum shown by a curve 4 in the figure), respectively, by fitting the absorbance values at each wavelength to the spectrum of the AS-DHFR. As shown in this figure, it was revealed by the measurement according to the present invention that the absorption spectra of the immobilized protein agreed very well with that of a solution of the protein. Further, it was revealed that the spectral intensity increased in proportion to the protein mass used for the immobilization and therefore the immobilized protein was able to be quantitatively measured. In addition, by using these values, the densities of the immobilized protein which was spotted using 0.5, 1, 2, and 4 µg of the AS-DHFR were estimated to be 0.11 µg/mm$^2$, 0.27 µg/mm$^2$, 0.50 µg/mm$^2$, and 0.85 µg/mm$^2$, respectively, by calculating them using 18000 as the molecular weight of the AS-DHFR. The spotted area was estimated to be about 4 to 5 mm$^2$.

In rough estimation based on the precision of the spectrophotometer used this time, the measurement can be performed by about one tenth of the above-mentioned signal intensity. Therefore, it is suggested that a protein can be sufficiently detected by 0.01 µg/mm$^2$ as a density of the immobilized protein in the protein array system according to the present invention.

The invention claimed is:

1. A system comprising (i) a protein array in which a protein is immobilized in aligned position on an ultraviolet light-transmissive substrate at a high density and (ii) a spectrophotometer, the system being for detecting or analyzing a protein on the protein array and/or a compound which is other than proteins and which interacts with the immobilized protein, wherein the protein on the protein array and/or the compound other than proteins are detected/analyzed by irradiating the protein array with ultraviolet light using the spectrophotometer, irradiating an ultraviolet-visible light converting device with the ultraviolet light transmitted through the protein array, and measuring the visible light converted from the ultraviolet light transmitted through the protein array for determining the light absorption of the protein on the array and/or the compound which is other than proteins and which interacts with the immobilized protein.

2. The system according to claim 1, wherein the protein is immobilized at a density of 0.01 µg/mm$^2$ or more per spot of the protein array.

3. The system according to claim 1, wherein the protein is immobilized at a density in such a manner that the absorbance of each spot of the protein array is 0.001 or more.

4. The system according to claim 1, wherein the protein immobilized in aligned position at a high density is represented by the formula $NH_2-R_1-CO-NH-R_2-CO-NH-Y$, wherein $R_1$ and $R_2$ each denote an optional amino acid sequence, and Y denotes a substrate.

5. The system according to claim 1, wherein the protein is immobilized in aligned position by a covalent bond between a carrier containing a primary amine cast on a surface of light-transmissive glass and a carboxy group at the C-terminus of the amino acid sequence of the protein.

6. The system according to claim 1, wherein the ultraviolet light-transmissive substrate is a quartz glass substrate.

7. The system according to claim 1, wherein the ultraviolet-visible light converting device is fluorescent glass.

8. The system according to claim 1, wherein a protein in a sample, the protein interacting with the immobilized protein, and/or a compound in a sample, the compound being other than proteins and interacting with the immobilized protein, is detected by bringing the sample into contact with the immobilized protein on the protein array and measuring the light absorption of the protein on the protein array and/or the compound which is other than proteins and interacts with the immobilized protein before and after the contact.

9. The system according to claim 1, wherein an interaction between the immobilized protein and another protein or a compound other than proteins is analyzed by bringing the another protein and/or the compound which is other than proteins and interacts with the immobilized protein into contact with the immobilized protein on the protein array and measuring the light absorption of the protein on the protein array and/or the compound which is other than proteins and interacts with the immobilized protein over before and after the contact.

10. The system according to claim 1, wherein the ultraviolet light-transmissive substrate is a flow channel cell or microchip provided with a channel therein, the protein is immobilized in the channel, and an interaction between the immobilized protein and a protein and/or compound in a sample, the compound being other than proteins and interacting with the immobilized protein, is analyzed by letting the sample flow in the channel.

11. A system comprising (i) a protein array in which a protein is immobilized in aligned position on an ultraviolet light-transmissive substrate at a high density, (ii) an ultraviolet light-irradiating means, and (iii) a light-detecting means, the system being for detecting or analyzing a protein on the protein array and/or a compound which is other than proteins and which interacts with the immobilized protein, wherein the protein on the protein array and/or the compound other than proteins are detected/analyzed by irradiating the protein array with ultraviolet light by the light-irradiating means; irradiating an ultraviolet-visible light converting device with the ultraviolet light transmitted through the protein array; and measuring the visible light converted from the ultraviolet light transmitted through the protein array by the light-detecting means for determining the light absorption of the protein on the array and/or the compound which is other than proteins and which interacts with the immobilized protein.

12. The system according to claim 11, further comprising a data-processing means.

13. The system according to claim 1, wherein the light-detecting means is a CCD or a photodiode array.

14. The system according to claim 11, wherein the protein is immobilized at a density of 0.01 μg/mm$^2$ or more per spot of the protein array.

15. The system according to claim 11, wherein the protein is immobilized at a density in such a manner that the absorbance of each spot of the protein array is 0.001 or more.

16. The system according to claim 11, wherein the protein immobilized in aligned position at a high density is represented by the formula $NH_2-R_1-CO-NH-R_2-CO-NH-Y$, wherein $R_1$ and $R_2$ each denote an optional amino acid sequence, and Y denotes a substrate.

17. The system according to claim 11, wherein the protein is immobilized in aligned position by a covalent bond between a carrier containing a primary amine cast on a surface of light-transmissive glass and a carboxy group at the C-terminus of the amino acid sequence of the protein.

18. The system according to claim 11, wherein the ultraviolet light-transmissive substrate is a quartz glass substrate.

19. The system according to claim 11, wherein the ultraviolet-visible light converting device is fluorescent glass.

20. The system according to claim 11, wherein a protein in a sample, the protein interacting with the immobilized protein, and/or a compound in a sample, the compound being other than proteins and interacting with the immobilized protein, is detected by bringing the sample into contact with the immobilized protein on the protein array and measuring the light absorption of the protein on the protein array and/or the compound which is other than proteins and interacts with the immobilized protein before and after the contact.

21. The system according to claim 11, wherein an interaction between the immobilized protein and another protein or a compound other than proteins is analyzed by bringing the another protein and/or the compound which is other than proteins and interacts with the immobilized protein into contact with the immobilized protein on the protein array and measuring the light absorption of the protein on the protein array and/or the compound which is other than proteins and interacts with the immobilized protein over before and after the contact.

22. The system according to claim 11, wherein the ultraviolet light-transmissive substrate is a flow channel cell or microchip provided with a channel therein, the protein is immobilized in the channel, and an interaction between the immobilized protein and a protein and/or compound in a sample, the compound being other than proteins and interacting with the immobilized protein, is analyzed by letting the sample flow in the channel.

* * * * *